United States Patent [19]
Maus et al.

[11] Patent Number: 5,738,658
[45] Date of Patent: Apr. 14, 1998

[54] HEAT-ACTIVATED DRUG DELIVERY SYSTEM AND THERMAL ACTUATORS THEREFOR

[76] Inventors: Daryl D. Maus, 3550 Smuggler Cir., Boulder, Colo. 80303; Scott F. Tibbitts, 8060 Niwot Rd. #298, Longmont, Colo. 80503

[21] Appl. No.: 483,145

[22] Filed: Jun. 7, 1995

Related U.S. Application Data

[62] Division of Ser. No. 110,876, Aug. 24, 1993, Pat. No. 5,505,706, which is a division of Ser. No. 524,218, May 15, 1990, Pat. No. 5,222,362, which is a continuation-in-part of Ser. No. 295,563, Jan. 10, 1989, abandoned.

[51] Int. Cl.$^6$ .................................................. A61M 5/00
[52] U.S. Cl. .................... 604/151; 604/151; 604/131; 60/527
[58] Field of Search .................... 60/527, 528, 530, 60/531; 604/131, 151, 155, 143, 132, 67

[56] References Cited

U.S. PATENT DOCUMENTS

| | | | |
|---|---|---|---|
| 3,121,331 | 2/1964 | Von Platen | 60/527 |
| 3,149,455 | 9/1964 | Daly et al. | 60/527 |
| 4,337,621 | 7/1982 | Lane, Jr. et al. | 60/527 |
| 4,668,220 | 5/1987 | Hawrylenko | 604/155 |
| 4,678,408 | 7/1987 | Nason et al. | 417/410 |
| 4,718,893 | 1/1988 | Dorman et al. | 604/67 |
| 4,744,786 | 5/1988 | Hooven | 604/143 |
| 4,769,008 | 9/1988 | Hessel | 604/132 |
| 4,772,263 | 9/1988 | Dorman et al. | 604/132 |
| 4,804,368 | 2/1989 | Skakoon et al. | 604/155 |

*Primary Examiner*—Sam Rimell
*Attorney, Agent, or Firm*—Parsons & Goltry; Robert A. Parsons; Michael W. Goltry

[57] ABSTRACT

A thermal actuator, also known as a heat capacitance motor, derives its energy from the physical expansion of paraffin wax as it changes from solid to liquid when heated within an enclosure such as a cylinder. This energy is converted into mechanical force which causes translation of a piston slidably mounted within the cylinder, thus creating hydrostatic pressure which is converted to work. The thermal actuator may be utilized in various drug delivery systems in which the hydrostatic pressure created by the actuator is used expel the contents of a syringe.

13 Claims, 16 Drawing Sheets

HEAT-ACTIVATED DRUG DELIVERY SYSTEM AND THERMAL ACTUATORS THEREFOR

BACKGROUND OF THE INVENTION

This application is a division of application Ser. No. 08/110,876, filed 24 Aug. 1993, now U.S. Pat. No. 5,505,706, which is a division of application Ser. No. 07/524,218 filed May 15, 1990, now U.S. Pat. No. 5,222,362, which is also a Continuation-In-Part of my U.S. Patent Application entitled "Thermostat Elements", filed Jan. 10, 1989 and assigned serial number 295,563, now abandoned.

Field of the Invention

This invention relates to drug delivery systems.

More particularly, the invention relates to ambulatory hypodermic infusion pumps.

In a further and more specific aspect, the invention relates to high-output paraffin thermal elements for actuating various medical infusion pumps.

Background of the Invention

Within the art of infusion pump technology, various drive mechanisms have been developed for driving the lead screw or syringe piston of the infusion pump. A primary objective the design of such mechanisms has been to make them compact and lightweight enough to be incorporated into the infusion pumps without seriously restricting the patient's freedom of movement, while still maintaining a high level of reliability and controlled, accurate delivery.

Among the various prior art mechanisms which have been proposed to meet this objective have been solenoid devices designed to create a pulsating pumping action. Other mechanisms utilize the force of tension springs. Still others use compressed gas as the driving force. Electric motors have also been used. One prior art device uses a latex bladder which has been prestressed to create a constant force and thus a constant infusion rate. While all of the above drive mechanisms provide novel and interesting solutions to some of the problems in making a compact, highly mobile infusion pump, none provide a complete system of solutions for all of the problems that arise under a variety of circumstances. For instance, most of the prior art drives are unable to ensure constant displacement regardless of force. Thus, variations in a patient's blood pressure, drops in fluid line pressure, and various other factors are likely to effect the flow rate of fluid being dispensed from the pump.

One type of mechanical force which has not, to date, been used for driving medical infusion systems is the force which can be derived from heat energy due to temperature changes. Devices for converting temperature changes into mechanical motion, often referred to as thermal actuators, are well known and are commonly found in such devices as fluid mixing valves, waterline thermostats, fire alarms and household zone valves.

One of the major problems in the design of prior art thermal actuators has been that the internal frictional forces have been high, leading to wear on the squeeze boot, loss of piston power, and large hysterisis. Since the frictional forces are proportional to the surface area of the actuator rod, one way of reducing these forces has been to limit the length of the actuator stroke. Consequently, actuators having strokes longer than 0.4" are not commercially available. Similarly, since both the external force and the frictional force on the rod increase as the square of the diameter of the rod, small diameter (ie. less than 0.125"), and hence, low output rods are also not available.

Still another problem of prior art actuators has been that it is not possible to repeatedly adjust the activation temperature of the thermal actuator after fabrication.

Another shortcoming of prior art thermal actuators has been the intrusion of outside materials into the interior of the boot. In the prior art, if the actuator is immersed in a pressurized fluid and left in the relaxed position for extended periods of time, the fluid can enter the space between the boot and the rod and shift the activation temperature.

All of the above shortcomings have made prior art thermal actuators unsuitable for use in medical infusion pump technology, which requires a higher output, longer strokes, and greater reliability that the prior art devices are capable of delivering.

It would be highly advantageous, therefore, to remedy the foregoing and other deficiencies inherent in the prior art.

Accordingly, it is an object of this invention to provide high output, long stroke thermal actuators which are suitable for driving a variety of medical infusion pumps.

Another object of the invention is to provide a family of infusion pumps which are capable of utilizing several sources of power such as rechargeable and disposable batteries, as well as ambient and patient body heat.

And another object of the invention is to provide an infusion pump motor which can be used with a variety of syringe types including disposable syringes.

Still another object of the invention is to provide an infusion pump motor capable of producing constant displacement regardless of force.

Yet another object of the invention is to provide a family of infusion pumps, all significantly smaller than conventional units to allow increased patient comfort and ambulatory freedom.

Yet still another object of the invention is the provision of an infusion system having improved safety features such as an occlusion alarm and direct visual verification of drug delivery.

And a further object of the invention is to provide a highly reliable and accurate infusion pump at reduced manufacturing costs.

And still a further object of the invention is the provision of an infusion system having simple mechanical prime and purge functions.

And yet a further object of the invention is to provide a tamper-resistant infusion system.

And still a further object of the invention is the provision of a user-operable infusion system capable of slow and smooth activation.

SUMMARY OF THE INVENTION

Briefly, to achieve the desired objects of the instant invention in accordance with the preferred embodiments thereof, a number of heat-activated infusion pumps are provided for meeting various different applicational requirements. Each of the pumps is driven by a thermal actuator, also known as a heat capacitance motor, which derives its energy from the physical expansion of paraffin wax as it changes from solid to liquid when heated within an enclosure such as a cylinder. This energy is converted into mechanical force which causes translation of a piston slidably mounted within the cylinder, thus creating hydrostatic pressure on the drug contents of the infusion pump and causing the drug to be expelled.

In one embodiment of the invention, the infusion pump is a miniature unit which can be worn on the patient's body, and which uses the patient's body heat as its power source.

In another embodiment of the invention, the infusion pump is a miniature, wearable unit in which the energy for melting the paraffin in the thermal actuator is supplied by resistance heating.

In other embodiments, the infusion pump is in the form of a larger capacity unit having control means for controlling the heat input, and thus the delivery rate of the system. In one case, the control means the heat input is a passive isothermal shell surrounding the actuator. In another case, the control means comprises an electronically regulated heater which maintains the shell surrounding the actuator at a desired temperature. In still another case, the control means comprises a thermistor array which measures the flux of ambient heat passing into the unit from the environment, and a microprocessor-controlled heater which is activated when the thermistors indicate that the ambient heat is insufficient. In another case, the control means comprises position sensing means which detects relative movement between the actuator and a surrounding body, and a microprocessor-controlled heater, the energy output of which is regulated by the position of the actuator. In yet another case, the control means comprises an insulation which varies in its resistance to heat transmission at a rate which is directly proportional to the fluctuations of ambient temperature.

Various embodiments of a thermal actuator usable with the infusion pumps of the present invention are also disclosed. Many of the embodiments include an improved squeeze boot which is designed to crease under pressure, thus defining a space for retaining lubricant along the length of the actuator rod. In addition, the geometry of the rod and of the squeeze boot when creased is selected to form a pocket of lubricant which follows the movement of the actuator rod, and to create a reservoir of lubricant at the opposite end of the boot. The reservoir releases lubricant over time as the size of the pocket decreases due to fatigue and compression set.

Several embodiments of the actuator also include adjustment means for varying the temperature at which the actuator rod begins to extend (ie. the activation temperature). For instance, in one embodiment, the adjustment means comprises an actuator plug movably mounted in the actuator body, at the end opposite the opening through which the actuator rod extends. An adjustment screw is provided for varying the position of the actuator plug, thus varying the volume available for expansion of the expansion material within the actuator body.

In another embodiment, the actuator plug is mounted in the same end of the actuator body as the actuator rod.

In yet another embodiment, the adjustment means comprises a second squeeze boot and a second actuator rod mounted at the opposite end of the actuator body from the first squeeze boot and actuator rod. The volume available for expansion of the expansion material within the actuator body varies as the position of the second actuator rod is changed.

In another embodiment of the invention, an actuator rod with an extra long stroke is provided.

In still another embodiment, the thermal actuator is provided with a remote sensing bulb.

In yet another embodiment of the invention, the thermal actuator is provided with an enhanced seal against water intrusion.

In two further embodiments of the invention, the thermal actuator is utilized in a solid state linear motor.

BRIEF DESCRIPTION OF THE DRAWINGS

The foregoing and other objects, features and advantages of the instant invention will become readily apparent to those skilled in the art from the following detailed description of the preferred embodiments thereof, taken in conjunction with the drawings in which:

FIG. 1B is a cross-sectional view through line A—A of the pump illustrated in FIG. 1a.

DETAILED DESCRIPTION OF THE PREFERRED EMBODIMENTS

Figure 1A:
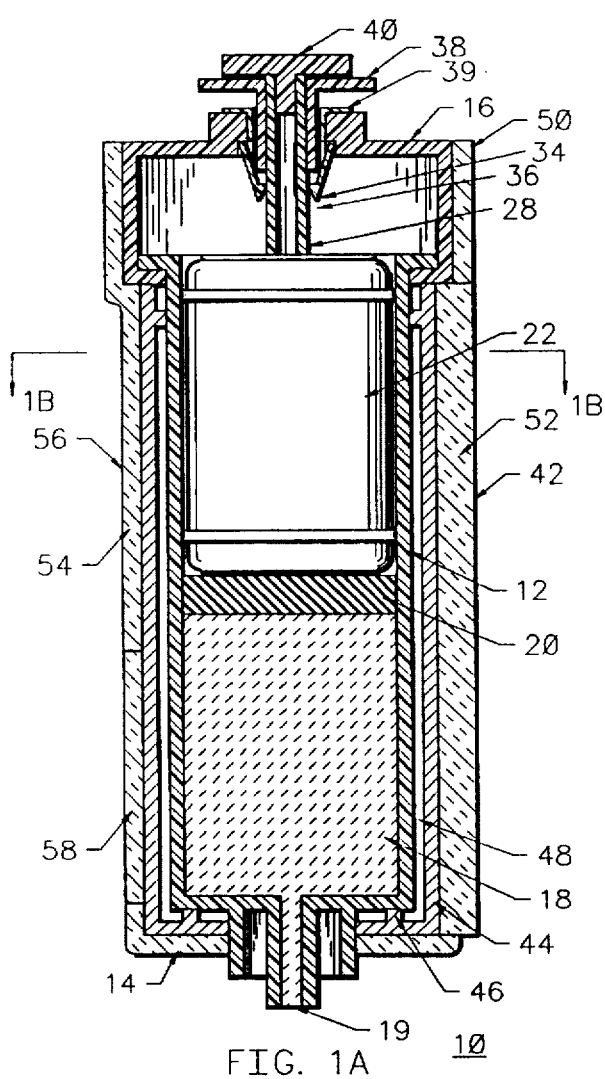
FIG. 1A is an axial sectional view of a body heat-powered infusion pump according to the present invention.
Figure 1B:
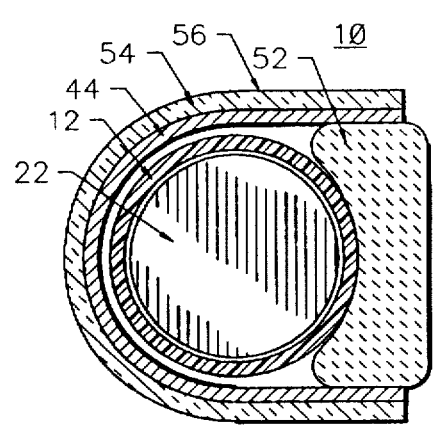

Turning now to the drawings, in which like reference characters indicate corresponding elements throughout the several views, attention is first directed to FIGS. 1A and 1B, which show a drug infusion system according to a first embodiment of the invention, generally indicated by the numeral 10. In this embodiment, the system is in the form of a wearable infusion pump which is powered by the patient's body heat and is designed to deliver dosages from three to ten ccs.

The infusion pump 10 comprises a disposable syringe 12 having a forward proximal end 14 and a rear distal end 16. A drug chamber 18 for storing prepackaged drugs is located in the forward portion of the syringe 12. The drug chamber has an outlet orifice 19 at its proximal end and is sealed at its distal end by a piston 20 slidably mounted in the syringe 12. Piston 20 contacts a heat capacitance motor 22, which is also mounted for slidable movement in syringe 12.

Figure 11:
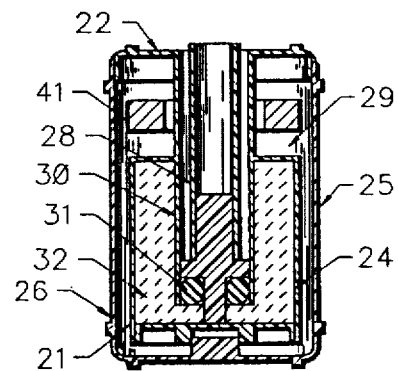
FIG. 11 is an axial sectional view through the heat capacitance motor uses in each of the pumps of FIGS. 1–10.

As illustrated in FIG. 11, heat capacitance motor 22 is a disposable molded plastic thermal actuator and insulation system including an outer shell 25 sealed to thermally conductive actuator body 24. The interior of actuator body 24 defines a chamber 26. An actuation rod 28 is mounted for reciprocation in the chamber 26. The actuation rod 28 is surrounded by a molded plastic sleeve 30. An O-ring 31 mounted in the open distal end of sleeve 30 sealingly engages the distal end of actuation rod 28. The annular space between sleeve 30 and actuator body 24 is filled with a thermally responsive material 32, such as paraffin, which expands on melting. The melting point of the material 32 is below the normal human body temperature.

A device known as a getter 41 is placed in vacuum chamber 29 in order to maintain the vacuum. Getter 41 is a ring formed of either barium or a zirconium-based alloy, the function of which is to collect any molecules which enter heat capacitance motor 22 through infiltration and/or outgassing, thus maintaining a nearly perfect vacuum (on the order of $10^{-5}$ Torr) and limiting heat transfer into the system. One getter which has been found suitable for use comprises a blend of zirconium, vanadium, iron, and nickel and is available as product number HS402 from Diversified Corporation of Colorado Springs, Colo.

Heat transfer is further reduced by applying a low emissivity coating to the inner surface of shell 25 and/or the outer surface of actuator body 24.

Turning now to FIGS. 1A and 1B, the rear end of actuation rod 28 extends through a spring-loaded, conical occlusion release latch 34, the proximal end of which includes inwardly projecting tabs 36 for frictionally engaging actuation rod 28. A bolus release 38, in the form of a hollow plunger, is carried in the distal end 39 of occlusion release latch 34, which is fixed to the rear end of the pump. An occlusion indicator 40, also in the form of a plunger, is carried in the distal end of bolus release 38.

Syringe 12 is enclosed by a multi-layered infusion pump body 42 comprising an isothermal shell 44, which encases all portions of syringe 12, except for the rear. Projections 46 formed on the inner surface of isothermal shell 44 keep the shell 44 evenly spaced from the syringe 12, thus creating a dead air space 48 around the syringe 12. The rear end of pump body 42 is sealed by an end cap 50.

One side of isothermal shell 44 contacts a liquid-filled heat conducting pad 52. The remainder of the shell is surrounded by a high R-value closed cell rigid insulation 54 such as polyisocyanurate, foam polyvinyl-chloride, or polyurethane. Insulation 54 is in physical contact with isothermal shell 44 and insulates shell 44 from the ambient environment. A polyvinyl-chloride jacket 56 envelopes insulation 54 and pad 52 to protect the assembly from physical abrasion. A viewing port 58 extends through jacket 58, insulation 54, and isothermal shell 54 to enable an observer to visually check the progress of drug delivery.

Operation of infusion pump 10 is as follows

The proximal end 14 of syringe 12, which has already been filled with the drug to be infused, is attached to an implanted catheter in the patient by connecting tubing (not shown). The infusion pump 10 is attached to the patient's arm at the infusion site by strapping or tape. Heat conductive pad 52 is placed against the patient's skin and, because it is liquid filled, conforms readily to the contour of the patient's limb, providing a comfortable fit as well as excellent thermal contact.

Immediately after contact with the patient's skin, pad 52 begins to conduct heat by fluidic convection and conduction to isothermal shell 44. Heat from isothermal shell 44 is prevented from significantly escaping to the atmosphere by insulation 54. Heat from isothermal shell 44 is slowly radiated and passes through dead air space 48 and syringe 12 into heat capacitance motor 22, which is initially in its unexpanded state. The rate of heat transfer into heat capacitance motor 22 is approximately 4.4 watts per minute with a heat flux of 0.0092 watts at delta T=60 degrees Fahrenheit. This causes the material 32 in heat capacitance motor 22 to expand. The expansion of material 32 is translated into axial force by the containment of the actuator wall 24. This axial force drives piston 20 at a controlled rate of 0.002 inches per minute into drug chamber 18, thereby causing the drug to be expelled through orifice 19.

Operation of the occlusion release system is illustrated in FIGS. 27 A–D. Should the drug delivery tube or catheter become blocked or occluded, the contents of drug chamber 18 will tend to exert a rearward force against piston 20 and heat capacitance motor 22. Normally, this force will be resisted by the frictional force exerted by tabs 36 of bolus release latch 34 against actuation rod 28, as shown in FIG. 27A. However, if the pressure within the system increases beyond a predetermined threshold level, for instance 10 psi, the frictional force of tabs 36 against rod 28 will be overcome, allowing rod 28 to extend rearwardly as shown in FIG. 27B, and stopping the build-up of pressure. The rearward movement of rod 28 will also force occlusion indicator 40 outwardly, thus visually warning the operator that the system needs to be checked. Occlusion release latch 34 can also be manually disengaged by pressing inwardly on bolus release 38, which causes tabs 36 to spring away from rod 28 as shown in FIG. 27C, allowing delivery of a bolus for prime or other purposes. When the syringe is initially filled, an excess volume of drug is included and the return plunger or occlusion indicator 40 is extended, which allows the user to manually purge or prime the tube by pushing down on plunger 40, as shown in FIG. 27D.

A second embodiment of the invention is illustrated in FIG. 2A–D. Once again, the system comprises a syringe 212 having a drug chamber 218 formed at its forward end. Drug chamber 218 has an outlet orifice at its proximal end (not shown) and is sealed at its distal end by a piston 220 slidably mounted in the syringe 212. Piston 220 is driven by a solid state linear pulse motor 221 carried by a specially configured crawler unit 223, the structure of which will be described below.

Pulse motor 221 comprises a heat capacitance motor 222, which is substantially identical in structure and function to heat capacitance motor 22 of the first embodiment, except that the heat for melting the paraffin or other thermal expansion material is generated by a resistor heating coil 225, rather than by the patient's own body heat. Thus, a higher melting point material may be used. Heating coil 225 is coupled to a control unit (not shown) by coiled electrical leads 227 passing through an orifice 229 in a cap 231 at the rear of syringe 212. The length of coiled leads 227 is sufficient to allow full extension of crawler unit 223 within syringe 212.

With additional reference now to FIGS. 3A–F, crawler unit 223 comprises a unitary assembly injection molded from a plastic or an elastomer such as synthetic rubber. The assembly includes a cylindrical central cradle 233, forward gripping unit 235, and rear gripping unit 237. Forward gripping unit 235 is attached to central cradle 233 by forward appendages 239, and rear gripping unit is attached to central cradle 233 by rear appendages 241. Forward appendages 239 are shaped into expandable and contractible springs.

Figure 3B:
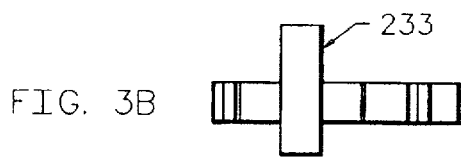
FIG. 3B is a side view of the crawler unit of FIG. 3A.
Figure 3A:
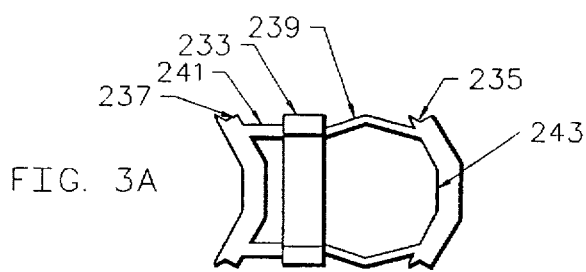
FIG. 3A is a top view of a crawler unit usable with the pump of FIGS. 2A–D.
Figure 3C:
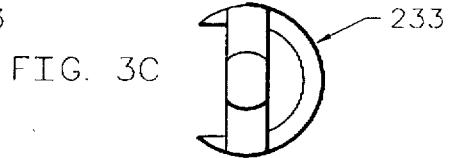
FIG. 3C is an end view of the crawler unit of FIG. 3A.
Figure 3E:
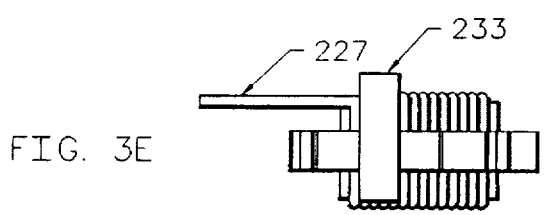
FIG. 3E is a side view of the solid state linear motor and crawler unit of FIG. 3D.
Figure 3D:
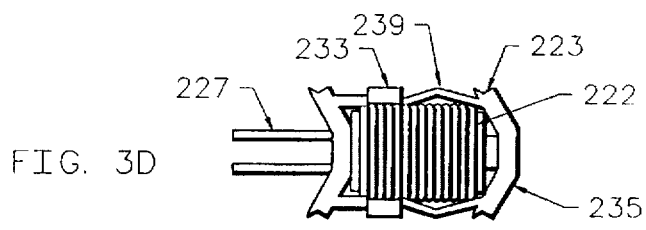
FIG. 3D is a top view, similar to FIG. 3A, showing a solid state linear motor mounted in the crawler unit.
Figure 3F:
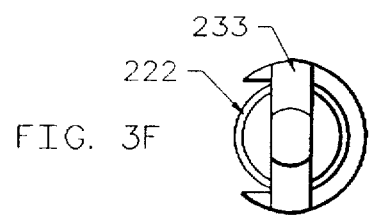
FIG. 3F is an end view of the solid state linear motor and crawler unit of FIG. 3D.

When heat capacitance motor 222 is inserted into crawler unit 223, as shown in FIGS. 3D–F, the motor is held in place by spring tension created by contraction of forward appendages 239, drawing forward gripping unit 235 toward rear gripping unit 237. Retention of heat capacitance motor 222 in crawler unit 223 is assisted further by girthing of cradle 233 about motor 222, and by an indent 243 in forward gripping unit, which receives the output shaft 228 of the motor 222.

Figure 2A:
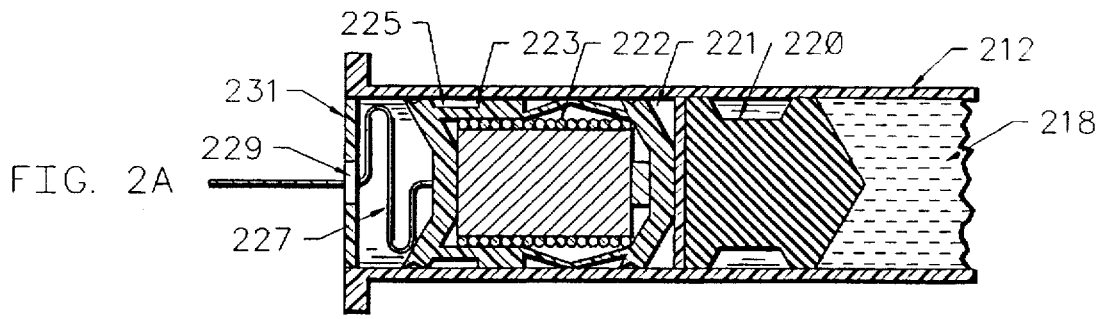
FIGS. 2A–D are fragmentary axial sectional views showing operation of a pulse infusion pump according to an alternate embodiment of the invention.

Referring again to FIGS. 2A–D, operation of the system is as follows:

Prior to actuation, crawler unit 223 is at the rear end of syringe 212, as shown in FIG. 2A. Output shaft 228 of motor 222 is in its unextended state. Both front gripper unit 235 and rear gripper unit 237 engage the inner cylindrical surface of syringe 212. Orifice 229 through syringe cap 231 allows crawler unit 223 and piston 220 to be manually pushed forward to allow purging of entrained air from syringe 212. Cap 231 prevents crawler unit 223 and piston 220 from being inadvertently removed.

Figure 2B:
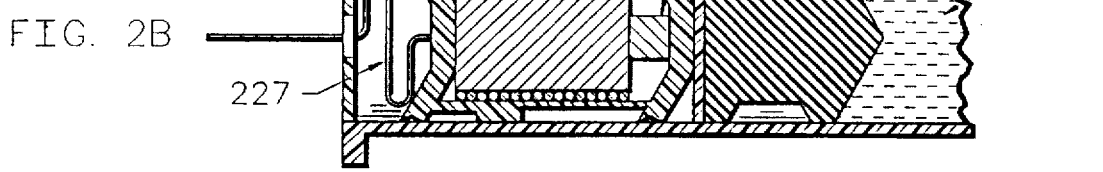

FIG. 2B shows the system during actuation of heat capacitance motor 222. A current of 0.1 watts is applied for 10 seconds through leads 227, generating resistance heat which causes volumetric expansion of the paraffin contained in heat capacitance motor 222, driving output shaft 228 against forward gripping unit 235. The rearward cant of forward gripping unit 235, as well as the structural weakness caused by piston indent 243, causes forward gripping unit 235 to release its grip on the wall of syringe 212, while rear gripping unit 237 continues to engage the wall. Thus, the forward force of shaft 228 causes forward gripping unit 235 to move forward and readily slide down the wall of the syringe, pushing piston 220 forwardly by precisely 0.02 inches. The hydraulic pressure generated by forward movement of the piston causes an exact dosage of 0.03 ccs to be dispensed from the syringe.

Figure 2C:
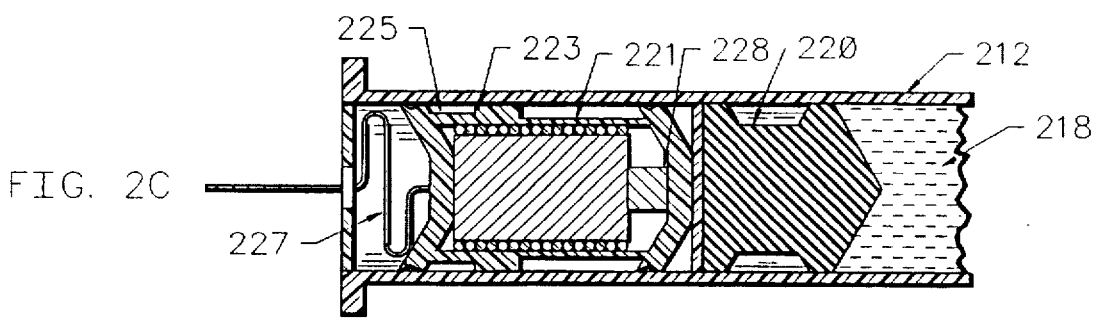

After heat capacitance motor 222 has been de-energized and allowed to cool for approximately one minute, plastic springs 221 contract against flaccid shaft 228, as shown in FIG. 2C. The rearward cant of rear gripping unit 237, as well as the structural weakness caused by a notch 245 in the unit 237, causes the rear gripping unit 237 to release its grip on the inner wall of the syringe 212, while front gripping unit 235 reengages the wall. This results in forward movement of rear gripping unit 237 and cradle 233 in syringe 12. The cylindrical shape of cradle 233 ensures that heat capacitance motor 222 is guided smoothly and coaxially down the shaft of the syringe. Retraction of shaft 228 equals its previous extension of 0.02 inches.

Figure 2D:
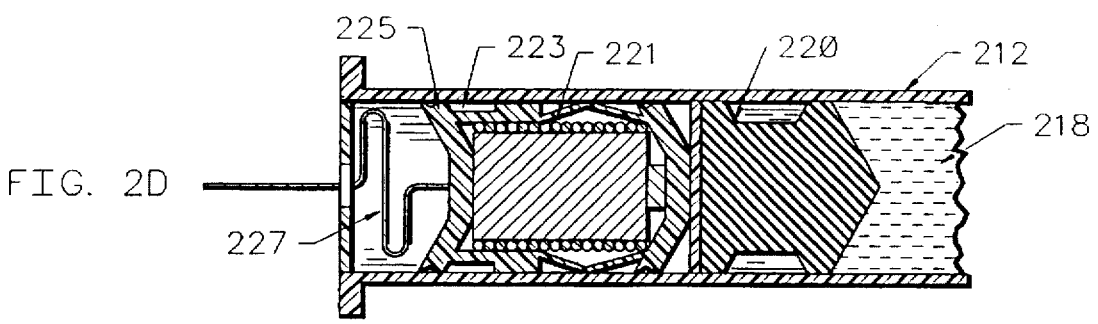

FIG. 2D shows crawler unit 223 advanced precisely 0.02 inches from its initial position, shown in FIG. 2A. Leads 227 have uncoiled to allow for the forward advancement. The total cycle time elapsed is one minute and ten seconds. The above listed steps of extending and retracting shaft 228 and advancement of crawler unit 223 are repeated until the supply of solution in drug chamber 218 has been exhausted.

Figure 4:
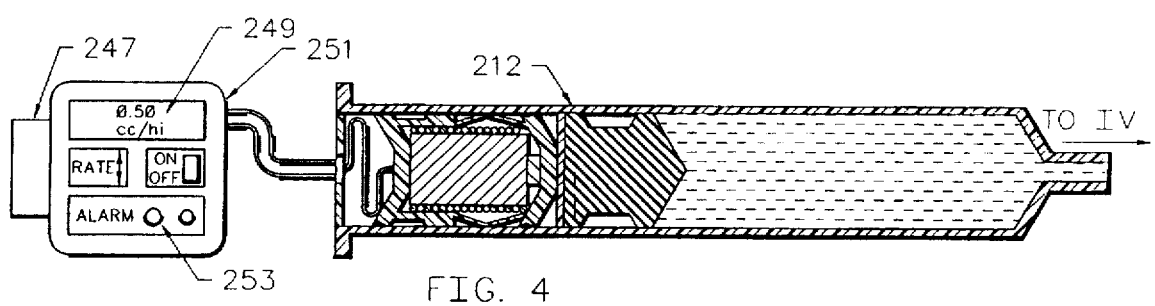
FIG. 4 is an axial sectional view of a portable wearable model of an infusion system incorporating the pulse infusion pump of FIGS. 2A–D.

FIG. 4 shows a portable/wearable model of the syringe 212 illustrated in FIGS. 2 and 3, in which the entire system is incorporated into a small, wearable package that can be carried in a belt or pocket, or in an arm or leg band which can be strapped onto the body near the I.V. site. The controller for the system is in the form of a miniature battery pack 247 which utilizes a simple timing circuit to provide pulses to the syringe 212. The number of pulses per hour determines the delivery rate of the syringe, which can be either pro-set or adjusted by the user, and which is displayed in a window 249 in the controller housing 251. Alarms 253 for warning the operator of line blockage, low battery, and other problems may also be included. A portable system using the miniature battery illustrated can operate for over 50 dispensing cycles before recharging or replacement of the battery is required.

Figure 5:
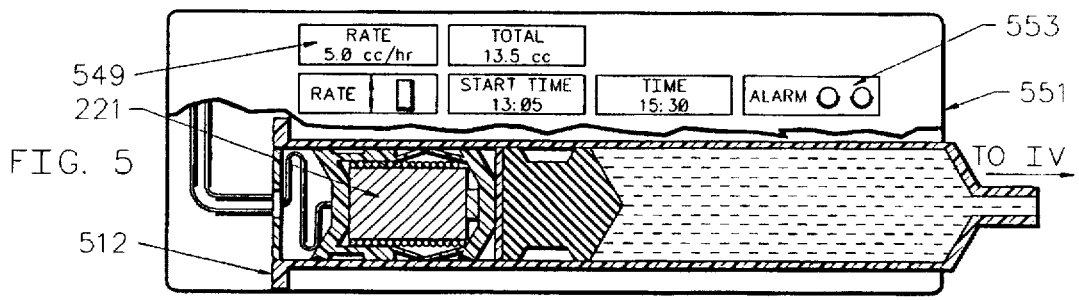
FIG. 5 is an axial sectional view of a bedside model of an infusion system incorporating the pulse infusion pump of FIGS. 2A–D.

A bedside model of the pulse infusion system illustrated in FIGS. 2 and 3 is shown in FIG. 5. In this model, which is appropriate for larger capacity syringes, syringe barrel 512 forms an integral part of controller housing 551. Power may be supplied by either a rechargeable battery or line power. Because motor 221 is contained with syringe barrel 512, the volume of the entire system is only approximately twice the volume of the syringe. This enables the system to be conveniently mounted in a variety of different arrangements, and reduces the amount of bedside clutter. As in the wearable model, a variety of optional features such as fluid delivery adjustment, display windows 549 and occlusion or battery check alarms 553 may be provided.

Figure 6:
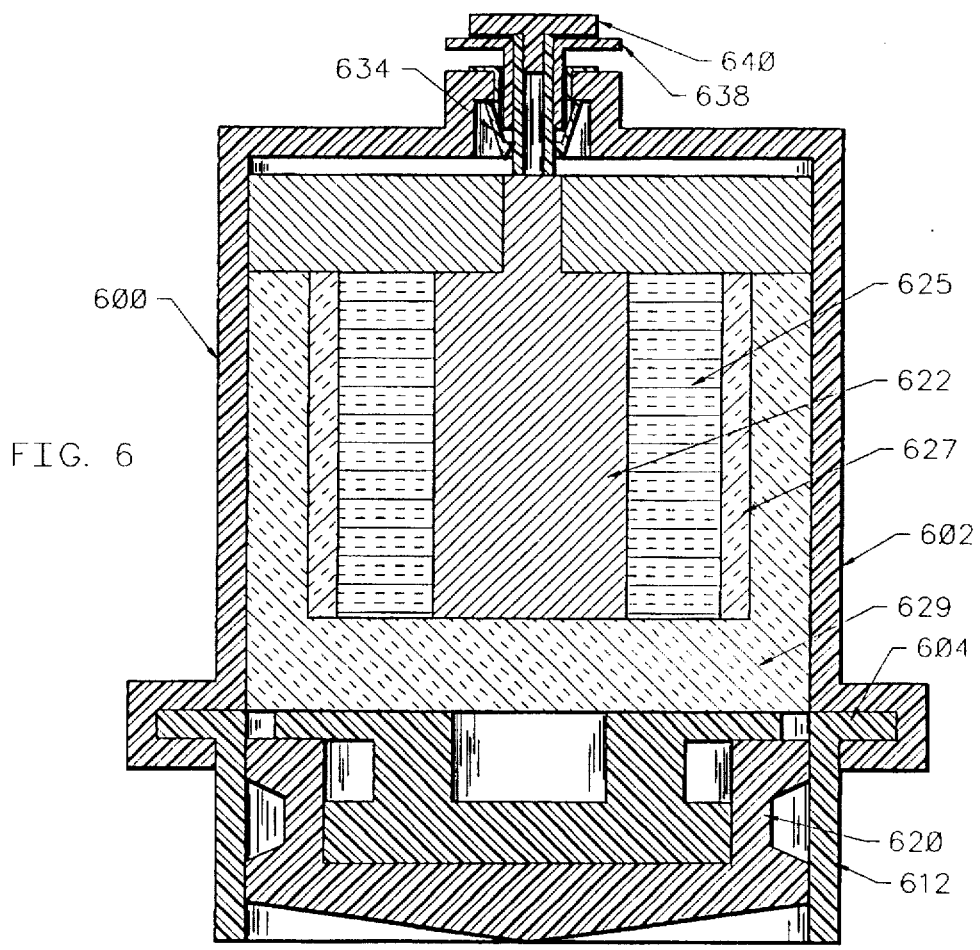
FIG. 6 is an axial sectional view showing an infusion pump according to another embodiment of the invention.

FIG. 6 illustrates an alternative infusion system designed to deliver dosages up to 100 ml. Like the system of FIGS. 1 and 2, this system is passive. In other words, no electrical heating is required. All the energy for driving the system is derived from environmental temperature changes.

More specifically, infusion pump 600 comprises a cylindrical drive body 602 coupled to the open top end of a syringe 612 by means of a locking bayonet flange 604. A heat capacitance motor 622 is mounted in the center of drive body 602. Heat capacitance motor 622 is similar to the motor illustrated in FIG. 11, with or without internal insulation except that the paraffin contained therein has a relatively low melting point, such as 45 degrees Fahrenheit. Motor 622 is surrounded by a layer of insulation 625 having a predetermined R-value and thickness. Insulation 625 is encased in an isothermal shell 627 formed of paraffin or similar material having a higher melting point than the paraffin in the heat capacitance motor 622. Isothermal shell 627 is concentrically surrounded by a layer of rigid insulation 629 such as polyisocyanurate. Heat capacitance motor 622, insulation 625, isothermal shell 627, and insulation 629 are mounted for movement in unison within drive body 602, and are operably connected to syringe piston 620. Also included with pump 600 are occlusion release latch 634, bolus release 638, and occlusion indicator or return plunger 640, all of which are identical to their counterparts in the first embodiment.

Operation of infusion pump 600 is as follows

Pump 600 is cooled before use to a temperature well below 45 degrees Fahrenheit. Normally, this requires a period of about 1 hour. Infusion pump syringe 612 is mated to pump body 602 by flange 604. Manual force is applied to occlusion indicator 640 while the assembly is held in an inverted position to purge the system of entrained air. After purging, syringe body 612 is connected to the patient by line and catheter (not shown). Ambient environmental heat passing through body 602 and insulation 629 heats wax 627 to its phase change temperature, where it remains throughout the operation of the system. Thus, heat flux through insulation 625 into heat capacitance motor 622 is constant, regardless of most variations in the environment, and is established primarily by the thermal resistance of insulation 625.

The heat transferred to heat capacitance motor 622 causes volumetric expansion the paraffin therein, which is translated into a linear drive force exerted on syringe piston 620. This results in linear displacement of piston 620, causing the drug contents of syringe 612 to be expelled. The rate of delivery from the syringe is slow and constant because of the constant heat transfer into the system, which was made possible by isothermal shell 627.

Figure 7:
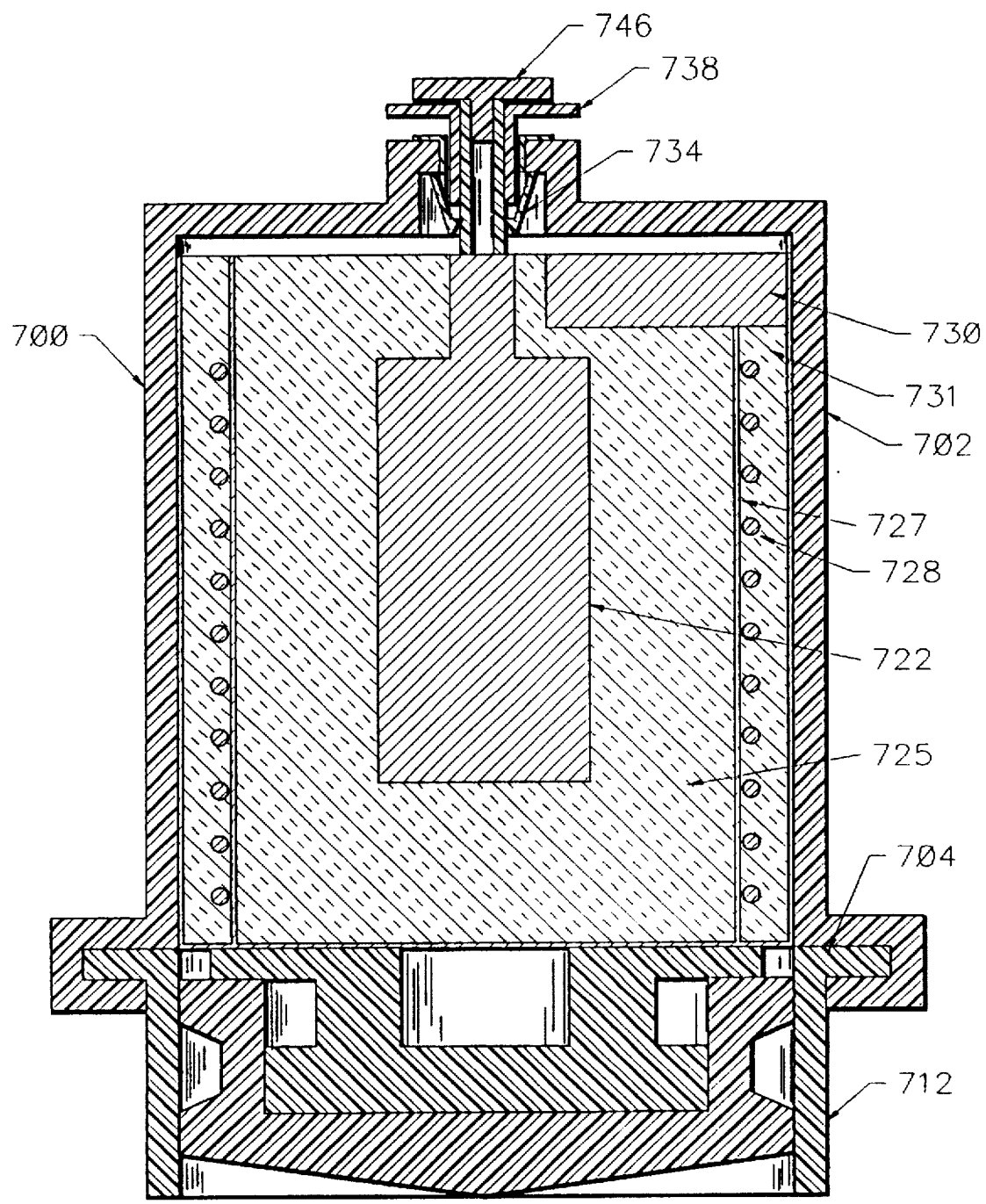
FIG. 7 is an axial sectional view showing an infusion pump according to yet another embodiment of the invention.

Another embodiment of the invention is illustrated in FIG. 7. Infusion pump 700 comprises a cylindrical drive body 702 coupled to the open top end of syringe 712 by means of a locking bayonet flange 704. Heat capacitance motor 722, which is similar in structure and function to the motor illustrated in FIG. 11, with or without internal insulation, is mounted coaxially within drive body 702. The paraffin wax inside heat capacitance motor 722 has a melting temperature above normal room temperature. A plurality of safety devices including occlusion release latch 734, bolus release 738, and occlusion indicator or return plunger 740, is carried in the rear end of drive body 702.

Heat capacitance motor 722 is encased in a layer of thermal insulation 725 which is surrounded by a temperature-regulating shell 727. Temperature-regulating shell 727 comprises a jacket formed of heat conductive material surrounded by resistance heating coils 728, which are connectedto a battery 730 mounted within drive body 702. Temperature regulating shell 727 is surrounded by a second layer of insulation 731.

Operation of this embodiment is substantially the same as in the embodiment of FIG. 6, except that it is not necessary to cool the unit before using, and that constant heat flux into the heat capacitance motor 722 is maintained by continuously supplying electrical energy to temperature regulating shell 727, rather than by passive means such as the paraffin jacket previously described.

Figure 8:
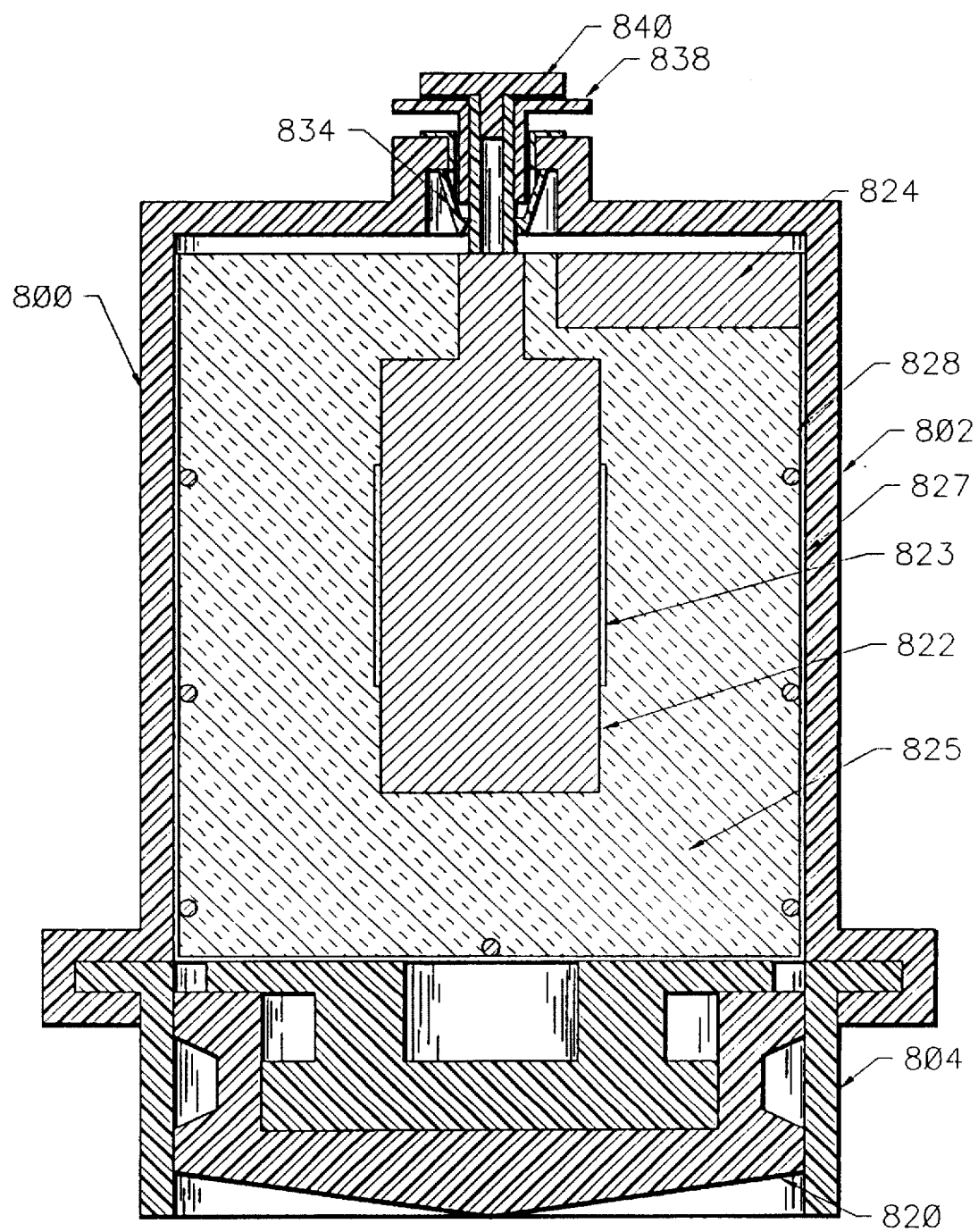
FIG. 8 is an axial sectional view showing an infusion pump according to still another embodiment of the invention.

Another embodiment of the invention is illustrated in FIG. 8. Infusion pump 800 of this embodiment includes a cylindrical drive body 802 coupled to the open top end of syringe 812 by means of a locking bayonet flange 804. Heat capacitance motor 822, which is similar in structure and function to the motor illustrated in FIG. 11, with or without internal insulation, is mounted coaxially within drive body 802. The paraffin wax inside heat capacitance motor 822 has a melting temperature of approximately 95 degrees Fahrenheit. A plurality of safety devices including occlusion release latch 834, bolus release 838, and occlusion indicator or return plunger 840, are carried in the rear end of drive body 802.

Heat capacitance motor 822 is in thermal contact with resistance heater 823, which is electrically connected to a microprocessor 824 mounted in drive body 802. Heat capacitance motor 822 and resistance heater 823 are surrounded by a layer of closed cell rigid insulation 825 such as polyisocyanurate or polyurethane. Insulation layer 825 is surrounded by a temperature-sensing shell 827 comprising a cylinder formed of heat conducting metal, such as brass: or aluminum, to which an array of spaced apart thermistors 828 are thermally bonded. Thermistors 828 are connected to microprocessor 824.

Operation of infusion pump 800 is as follows

Drive body 802 and all its contents are thoroughly cooled at room temperature until the actuator is fully retracted. After cooling, element 802 is mated to syringe 812 by mounting flange 804. Syringe 812, having been prefilled with the drug to be infused, is purged of air by applying manual pressure to plunger 840 while element 802 and syringe 812 are held in an inverted position. After purging, syringe 812 is connected to the patient by line and catheter (not shown). Ambient environmental heat passing through drive body 802 and shell 827 causes a proportional electrical resistance change in thermistor array 828. The electrical resistance change in thermistor array 828 is sensed, averaged, and translated by microprocessor 824. Microprocessor 824 energizes resistance heating element 823 intermittently and in accord with a linear or logarithmic relationship pre-programmed into the read-only memory of microprocessor 824. Heating element 823 supplies supplemental heat to augment the thermal flux passing through insulation 825 into the system from the ambient environment. Insulation 825 provides thermal resistance to the heat flow, preventing too rapid activation of heat capacitance motor 822. The combined heat energy provided by heater 823 and ambient thermal flux provide steady and continuous heating of the wax inside heat capacitance motor 822. The wax expands as heated, causing movement of heat capacitance motor 822, insulation 825, and shell 824 relative to drive body 802, thereby exerting pressure on syringe piston 820, causing the contents of syringe 812 to be expelled at a constant rate.

Figure 9:
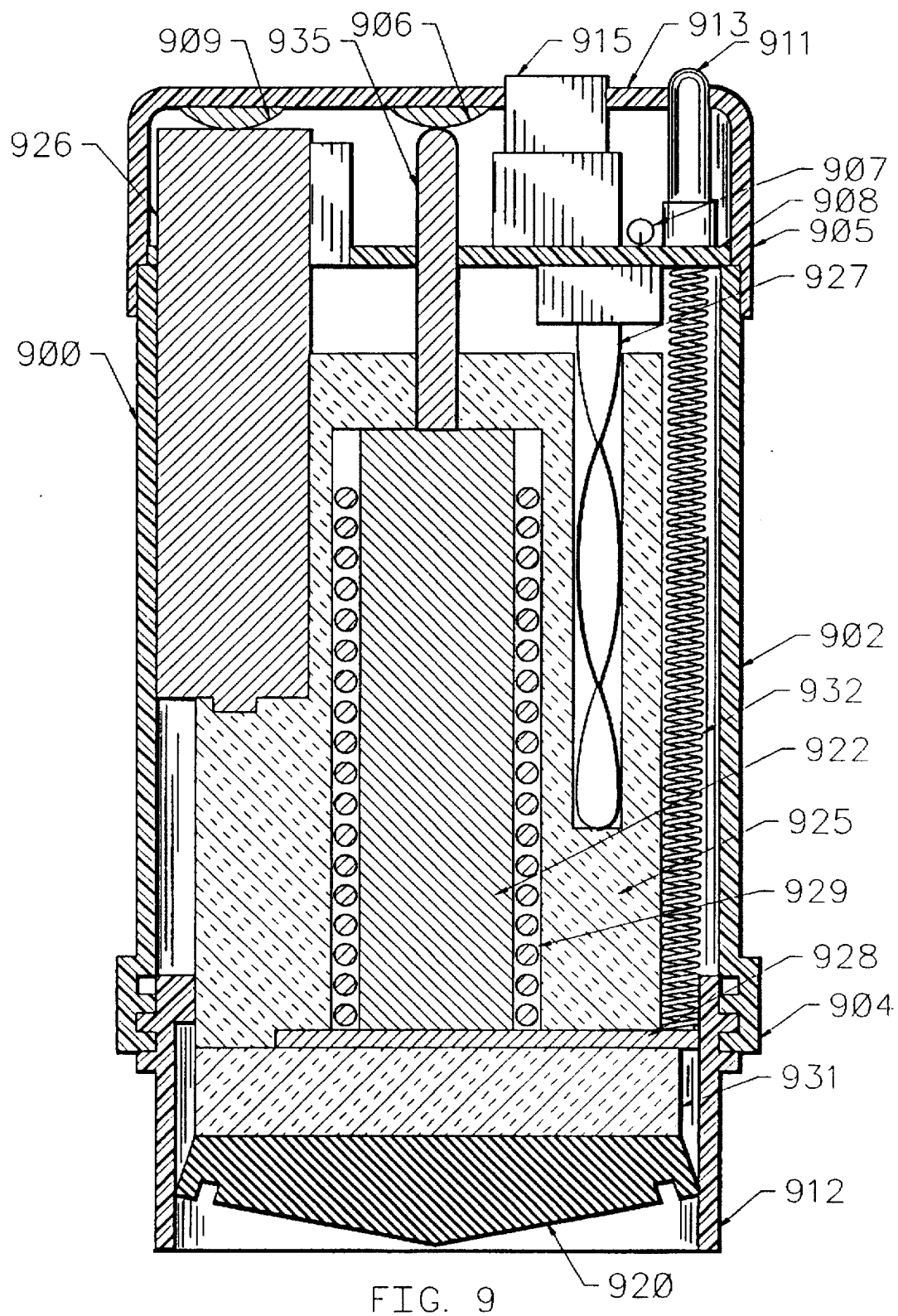
FIG. 9 is an axial sectional view showing an infusion pump according to yet still another embodiment of the invention.

Still another embodiment of the invention is illustrated in FIG. 9. The infusion pump 900 according to this embodiment includes a drive body 902 mounted to a syringe portion 912 by bayonet mount 904. The rear end of drive body is fitted with a cap 905. Cap 905 contains an occlusion switch 906, a plurality of electrical control components 907 mounted on a circular electrical circuit board 908, and a battery contact 909. Board 908 is held captured between cap 905 and the rear of drive body 902. Electrical control components 907 include an LED inclusion indicator 911 which is mounted to pass through an aperture in cap 905, a piezoelectric occlusion alarm 913, and an adjustable trim pot 915.

The interior space of body 902 contains a cylinder of rigid insulation material 925 such as polyurethane or polystyrene. Insulation 925 is shaped to contain a battery 926, a linear-to-rotary position encoder 927, and a heat capacitance motor 922 similar to the motor shown in FIG. 11, with or without internal insulation, but containing a wax of relatively high melting point—for instance, 95 degrees Fahrenheit. At the base of heat capacitance motor 922 is located a heat sink 928. In addition, heat capacitance motor 922 is surrounded by heating coils 929. Beneath heat sink 928 are located syringe insulation 931 and syringe piston 920. A return spring 933 is connected to heat sink 928.

Operation of this embodiment is as follows

Since the melting temperature of the wax used in heat capacitance motor 922 is relatively high (95° F.), it is necessary to cool the system 900 only if ambient temperatures are very high. Prior to use, the drive body 902 is mounted to syringe 912 by mounting flange 904. Syringe 912 has previously been filled with the drug to be infused. Turning the threaded mating flange interlock 904 one half turn purges the system of fluid. Syringe 912 is connected to the patient by a line and catheter (not shown), thereby placing the system into operation. Delivery rate is adjustable and selectable by manually turning trim pot 915. Rotation of the trim pot 915 is sensed by a microprocessor mounted on board 908. Electrical current from battery 926 flows to electrical heating coil 929 mounted on heat capacitance motor 922. This causes the wax in motor 922 to expand at a rate proportional to the electrical current applied to heating coil 929. Insulation 925 and 931 prevent unwanted thermal leakage to the environment. As the wax expands, force is applied to piston shaft 935, which exerts force against occlusion switch 906. If the force exceeds 12 psi, switch 906 closes, which activates one of the LED indicators 911 and causes alarm 913 to sound. If the force is less than 12 psi, the occlusion warning system is not activated.

Reactionary force between heat capacitance motor 922 and shaft 935 causes heat capacitance motor 922, insulation 925 and heat sink 928 to move against the force of spring 933, thus moving piston 920 and expelling any drug contained in syringe 912. If linear-to-rotary position encoder 927 senses that movement of the elements is too rapid, coil 929 is de-energized. The coil is alternately energized and de-energized by the microprocessor in response to feedback received from the encoder 927, causing piston 920 to move at a constant rate.

To reset motor 922, syringe 912 is removed and heat sink 928 is exposed to the environment, causing excess heat to be dissipated This causes the contents of drive body 902 to be retracted by spring 933, in preparation for another use.

This embodiment of the invention is intended for re-use, and may incorporate a counter which allows the user to determine when the recommended number of cycles has been reached and the useful life of the system has been exhausted.

Figure 10:
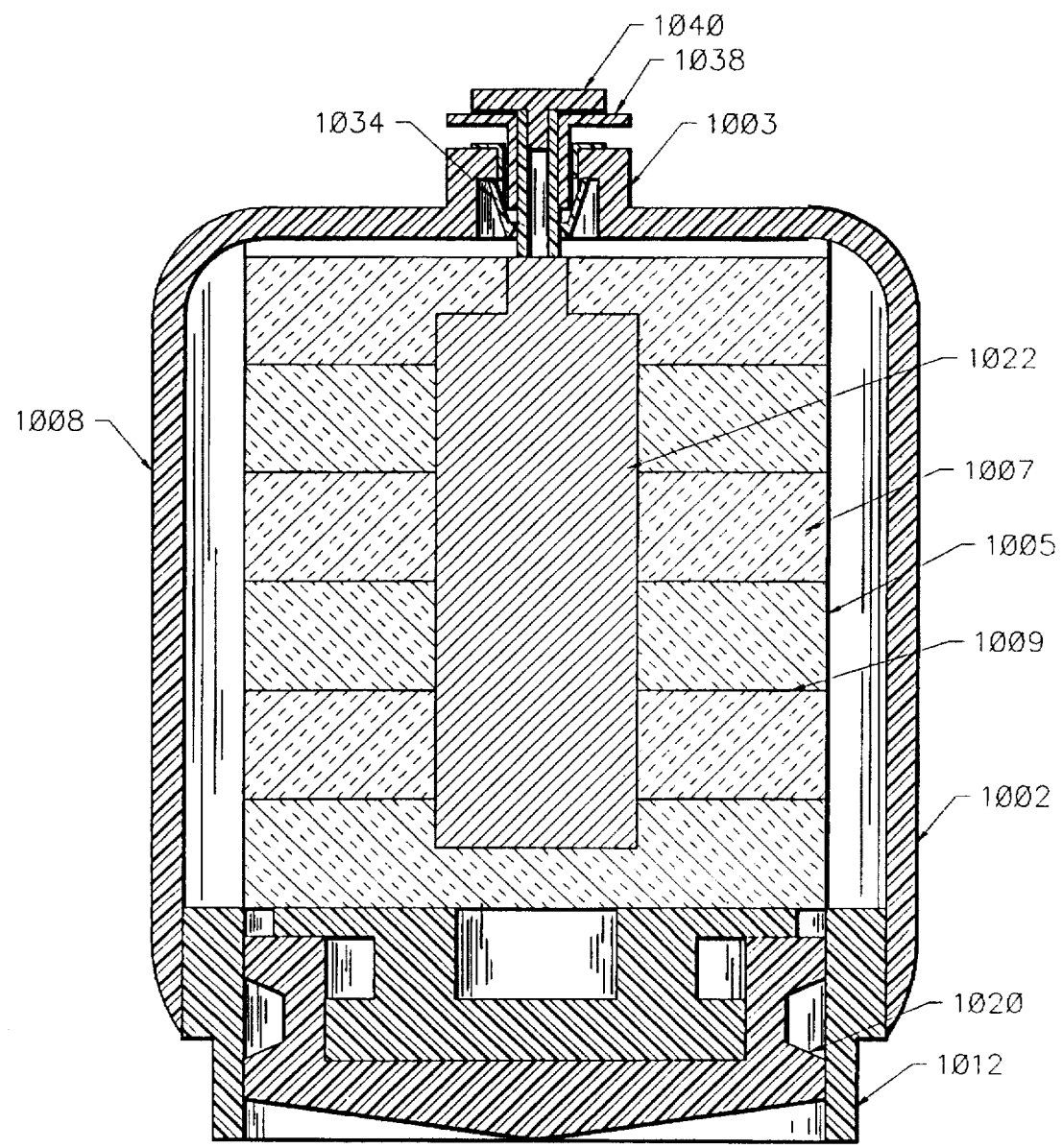
FIG. 10 is an axial sectional view showing an infusion pump according to another alternative embodiment of the invention.

Yet another embodiment of the invention is illustrated in FIG. 10. In this embodiment, infusion system 1000 includes drive body 1002, which is formed to attach to a preloaded syringe 1012. Syringe 1012 contains a piston 1020. An orificed mount 1003 is provided centrally of the rear end of drive body 1002. Occlusion release latch 1034, bolus release 1038, and occlusion indicator or return plunger 1040 are carried in orificed mount 1003. Heat capacitance motor 1022, which is similar in structure and function to the motor illustrated in FIG. 11, with or without internal insulation, is mounted coaxially within drive body 1002.

Heat capacitance motor 1022 is encased in a thermal governor 1005, which comprises a stack of annular pieces of expandable insulation 1007. When the unit is chilled, the individual pieces of insulation 1007 are in an unexpanded state, which creates gaps 1009 between neighboring pieces of insulation 1007, allowing ambient air and heat to reach heat capacitance motor 1022. Heat capacitance motor 1022 is rapidly warmed, causing the wax contained within to expand. This, in turn causes piston 1020 to move within syringe 1012, expelling the contents of the syringe 1012. The rapid initial heating of motor 1022 enables a health care professional to quickly ascertain whether the system is operating correctly.

As the system heats, insulation sections 1007 are also heated, which causes them to expand and seal the gaps 1007 between adjacent sections. This sealing reduces heat flow to heat capacitance motor 1022, so that the only available heat flow is that which is available as conductive energy through sections 1007. If the ambient temperature decreases, sections 1007 will again cool and contract causing the thermal resistance of thermal governor 1005 to decrease. Thus, the insulating ability of governor 1005 varies directly in proportion to any fluctuations in ambient temperature. As a result, both the heat flux into the system and the rate at which drugs are dispensed from syringe 1012 are essentially constant.

Because it does not require any artificially generated energy (ie. electricity), and because of its rapid actuation time, infusion system 1000 is especially suitable for emergency use, such as would be required by medics on the battle field or by paramedics responding to accidents.

Each of the infusion pumps illustrated in FIGS. 1–10 is intended to be used only once or a limited number of times and then disposed of. For this reason, the heat capacitance motors used in each of these pumps comprise relatively simple, inexpensive thermal actuators having short service lives. However, in certain circumstances, longer lasting, reusable infusion systems may be preferred. In such circumstances, more durable actuators are required. Accordingly, a number of actuators which would be suitable for long-term use are illustrated in FIGS. 12–25.

The embodiment of FIGS. 12–15 comprises an actuator body 1210, which may be tubular in shape. The actuator body 1210 may be made of any thermally conductive, high strength material such as copper or stainless steel. A cylindrical actuator piston 1211 seals one end of the actuator body 1210, along with an O-ring 1212 and an O-ring backup 1213. A cylindrical actuator plug 1214, a cylindrical actuator boot 1215, and backup ring 1219 seal the opposite end of the actuator body 1210. The enclosed volume is filled with a thermally responsive material 1216, such a paraffin fusion charge, that expands on melting. An actuator rod 1217 passes through the actuator plug 1214, into the cylindrical cavity in the actuator boot 1215, and is free to move with respect to both the actuator boot 1215 and the actuator plug 1214. The interface between the actuator rod 1217 and the actuator boot 1215 is lubricated by a lubricant 1218.

The temperature at which the actuator rod 1217 begins to extend is determined by the volume available for expansion of the thermally responsive material 1216, which in turn is determined by the position of the actuator plug 1211 with respect to the actuator body 1210. This position may be established by various means, some of which will be described later with respect to the embodiments of FIGS. 15, 23, and 24.

With the exception of the actuator boot 1215, the O-ring 1212, and the O-ring backup 1213, the elements of the actuator can be fabricated from any suitable metallic material such as brass, copper, or stainless steel. In the preferred embodiment, the actuator boot 1215 is fabricated from a high tear strength polyurethane thermoset or thermoplastic elastomer having a Shore A durometer rating of 75–85 and high compression set. However, other suitable elastomeric materials capable of transferring hydraulic forces to the actuator rod 1217 could also be used.

Figure 13:
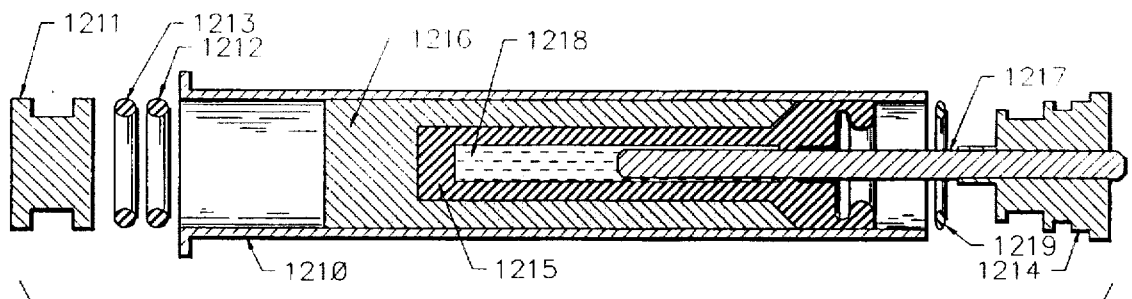
FIG. 13 is a sectional view of the thermal actuator of FIG. 12, showing the components before assembly.

Referring now to FIG. 13, the primary embodiment of the invention is shown prior to assembly. It can be seen that the components are assembled in the following order: first, the backup ring 1219, which accommodates wide and easy-to-manufacture tolerances in the tube 1210, and the actuator boot 1215 are assembled on the actuator plug 1214, which is then inserted into the actuator body 1210 and crimped into place. Next, the actuator is charged with paraffin 1216, and the actuator piston 1211, the O-ring 1212, and the O-ring backup 1213 are inserted in the other end of the actuator body 1210. Because the actuator is adjustable, calibration is generally not required. However, if it is required, the finished actuator is fixtured and the tube wall dimpled as necessary.

Figure 12:
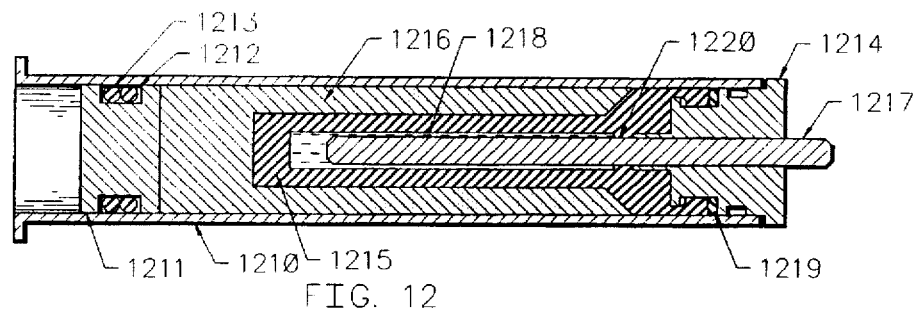
FIG. 12 is a sectional view through a thermal actuator usable with the infusion pumps according to the present invention.
Figure 14:
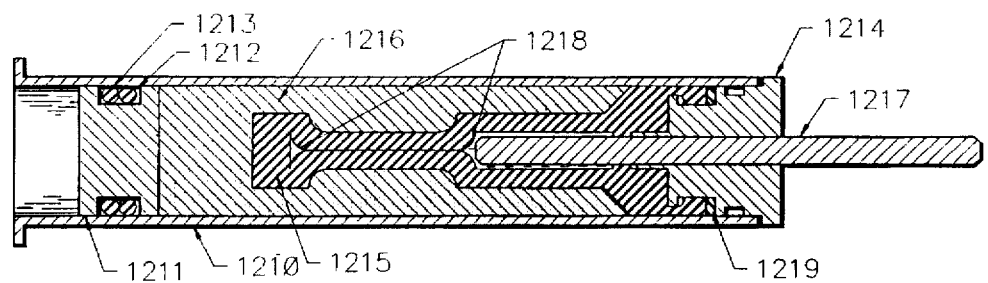
FIG. 14 is a sectional view of the thermal actuator of FIG. 12, showing the actuator rod extended after heating.

In operation, the actuator rod 1217 takes the position shown in FIG. 12 when the thermally responsive material 1216 is in the contracted position (ie. below the actuation temperature). On heating, the material 1216 begins to melt and expand, creating hydraulic pressure that causes the actuator boot 1215 to compress around the actuator rod 1217, causing the rod 1217 to extend from the actuator, creating mechanical work that is available for a control system. Heating can be provided by any suitable means such as exposing the actuator to a warm environment or electrical resistance heating, with either an external or internal resistance element. In a typical application, the actuator extension is opposed by a return spring (not shown), which provides a retracting force upon cooling. FIG. 14 shows the actuator rod 1217 in the extended position after the expansion of the thermally responsive material 1216 has forced the actuator rod 1217 to full extension. As the actuator 1216 cools, the thermally responsive material 1216 contracts and the actuator rod 1217 is retracted into the actuator under the action on the return spring (not shown).

FIGS. 15a–e show longitudinal and lateral cross sections of the invention in operating and relaxed position. The distribution of forces is shown. The relationships shown were discovered using unique transparent elastomers operated in pressure chambers, allowing viewing of the actuator function.

Figure 15A:
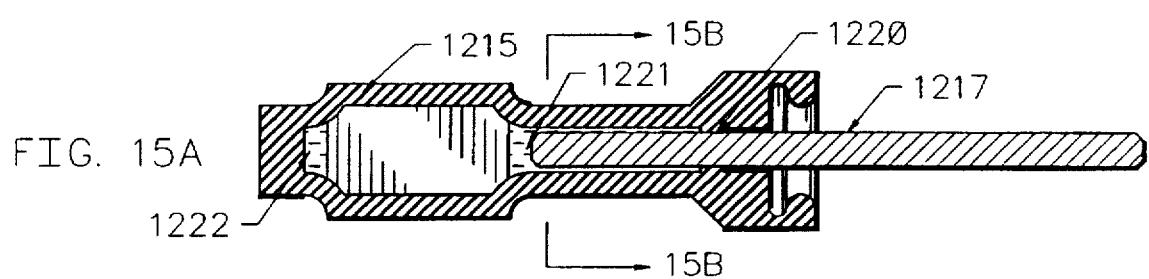
FIGS. 15 A–E show longitudinal and lateral views of the actuator in operating and relaxed positions.
Figure 15B:
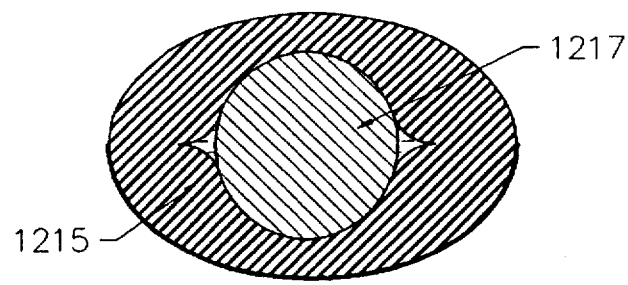
Figure 15C:
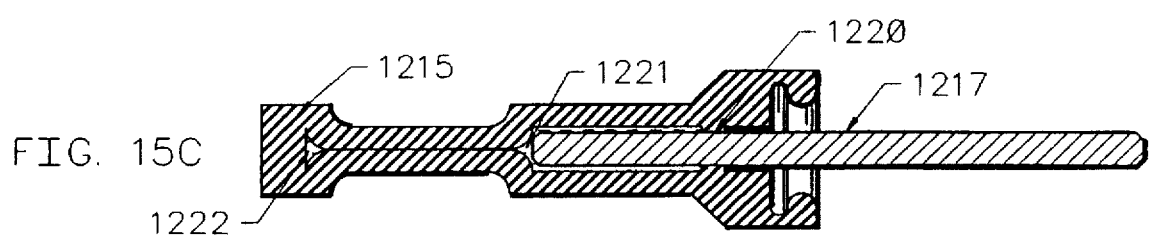
Figure 15D:
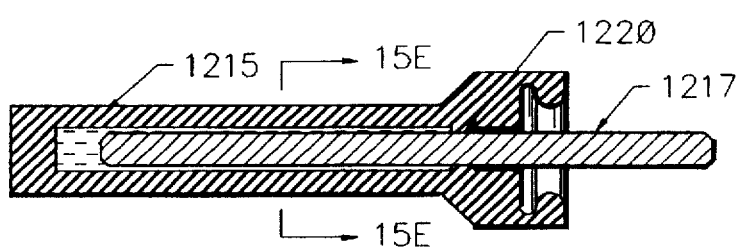
Figure 15E:
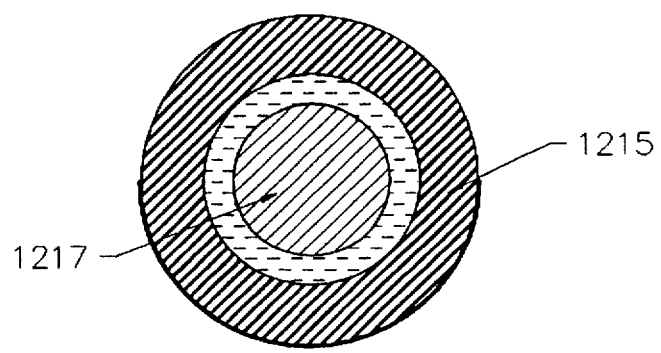

A critical factor in the actuator's ability to retain and distribute lubricant 1218 in the annular space between the rod 1217 and the squeeze boot 1215 is its ability to crease as shown in FIG. 15B. This creased configuration reduces the area of contact between the actuator rod 1217 and the boot 1215. Since the total frictional force acting on the rod 1217 is a product of the surface area and the coefficient of friction (which is affected by the availability of lubricant 1218), the frictional force is reduced by this design.

Additionally, the invention utilizes the geometry of the rod 1217 and of the boot when creased to form a pocket 1221 of lubricant at the end of the rod. This pocket 1221 follows the rod like a "tail", relubricating the boot surfaces and distributing lubricant as the rod 1217 moves in and out. A reservoir 1222 of lubricant is also created at the opposite end of the boot 1215. Compression set in the boot 1215 causes the volume of reservoir 1222 to shrink over time, thereby expelling the lubricant it initially contained into the annular space between the rod 1217 and the boot 1215 to replace any lubricant which may have been lost. Optimization of the boot geometry as well as the characteristics of the elastomer, such as compression set, allow the release of lubricant to be extended over time, thereby significantly extending the cycle life of the actuator.

The ability of the boot to crease as shown is dependent on the relationship between the boot durometer and wall thickness, and on the size of the annular space between the boot 1215 and the rod 1217. For example, in one preferred embodiment of the invention, the actuator includes a rod 1217 having a diameter of 0.70", and a boot 1215 having an inner diameter of 0.093", an outer diameter of 0.200", and a Durometer of 80 Shore A. An actuator according to this embodiment has established life cycles as high as 400,000, stroking for 0.8". This general relationship holds true proportionally for other sizes (with the application of empirically obtained size coefficients). Actuators up to 3" in length have been built and operated using this relationship.

Figure 16A:
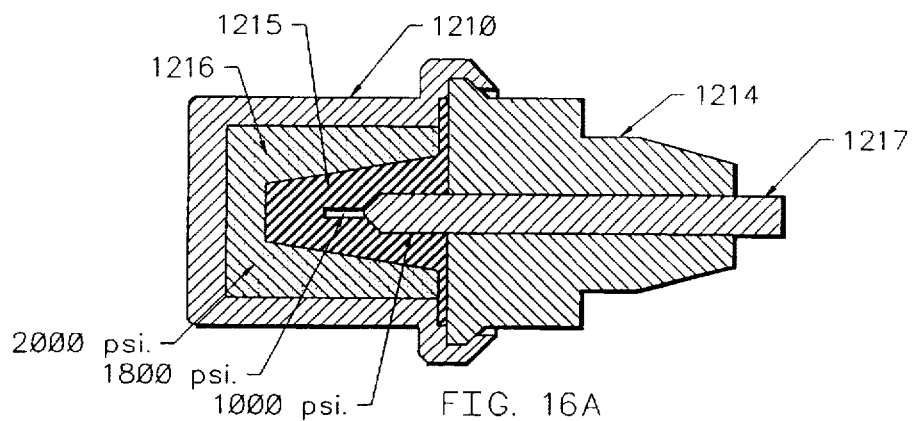
FIG. 16A and B show a comparison between a prior art thermal actuator and a thermal actuator according to the present invention.
Figure 16B:
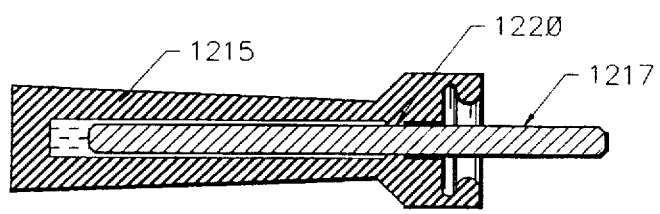

Another feature of the present invention is that the actuator boot is straight or tapered toward the front, as shown in an exaggerated fashion in FIG. 16B. This is the opposite of conventional boot design, which is tapered toward the rear, as shown in FIG. 16A. Unlike the prior art design, which creates a pressure differential, promoting the loss of lubricant from the front end of the boot, the present design actually improves lubricant retention and increases the life of the actuator.

Still another important feature of the invention is its molded-in wiper ring 1220, which promotes centering of the rod 1217 in the boot 1215 so that it creases as required. This wiper ring also seals the boot, promoting the retention of lubricant and preventing intrusion by outside materials. The seal provided by the molded wiper ring 1220, which utilizes the elastic memory of the boot material, typically withstands pressures up to 80 psi.

Figure 17:
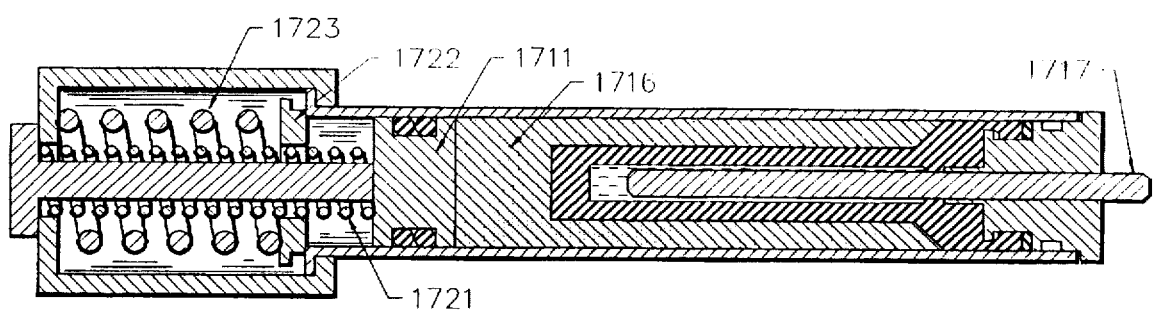
FIG. 17 is a sectional view of an alternative embodiment of a thermal actuator according to the present invention

FIG. 17 shows a mechanism for adjusting the position of the actuator piston 1711 in relation to the actuator body 1710, and thus, the temperature at which the rod 17 begins to extend. The actuator plug 1711 is held in place by an adjustment screw 1721. The adjustment screw 1721 is threaded through an adjustment nut 1722 such that, as the adjustment screw 1721 is turned, the position of the actuator plug 1711 is adjusted, varying the volume available for expansion of the thermally responsive material 1716. Increasing the available volume increases the actuation temperature. More room is available for expansion, and a larger degree of expansion must occur before hydraulic pressure is available to move the actuator rod 1717. By the same logic, decreasing the available volume decreases the actuation temperature.

FIG. 17 also illustrates an overtravel protection device. The adjustment nut 1722 is held in place by overtravel springs 1723, which are compressed to the point that they provide a high degree of resistance to the movement of the actuator piston 1711. As the thermally responsive material 1716 expands, the overtravel springs 1723 prevent movement of the actuator piston 1711 until the actuator rod 1717 has fully extended. If the temperature of the actuator is increased further, the increased hydraulic pressure causes the actuator piston 1711 to move against the overtravel springs 1723, preventing damage to the actuator from excessive hydraulic pressures. On cooling, the actuator piston 1711 moves back into the nominal position, and the actuator rod 1717 retracts in the normal manner.

Figure 18:
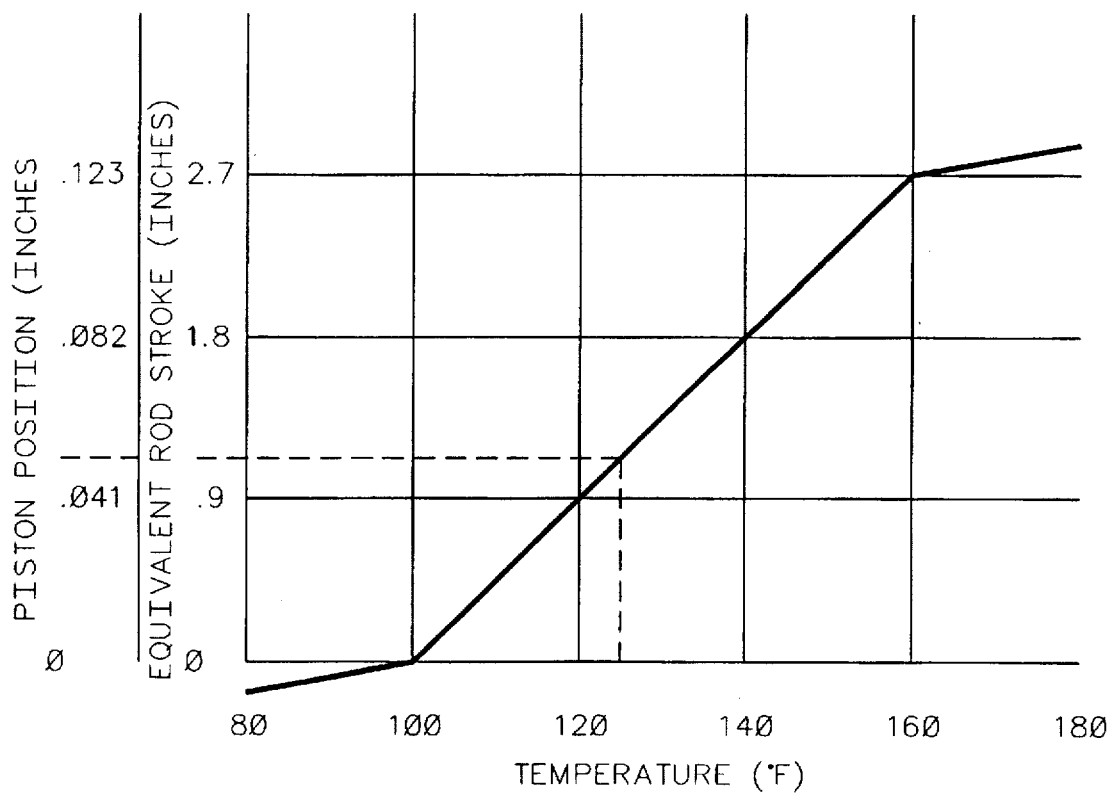
FIG. 18 is a graph illustrating the interrelationship of temperature, piston position, and actuator rod stroke in a preferred embodiment of the invention.

The relationship of piston position, temperature, and rod stroke in a preferred embodiment is shown in FIG. 18. The actuator temperature is plotted on the horizontal axis, while piston position and rod stroke are plotted on the vertical axis. From the graph, it can be seen that if the actuator piston is positioned at 0.50" from the open end of the actuator body, the wax expands to the available volume at a temperature of 125 degrees Fahrenheit. At this temperature, the expanded wax will begin to act on the actuator rod, forcing it to extend. The rod will continue to extend until the limit of its stroke, at which time any further expansion will act on the piston, forcing it out. It can be seen that by varying the position of the piston, the temperature at which the rod will move can be varied. This feature allows for an adjustable temperature of actuation, and calibration of the actuator after assembly and installation.

Figure 19:
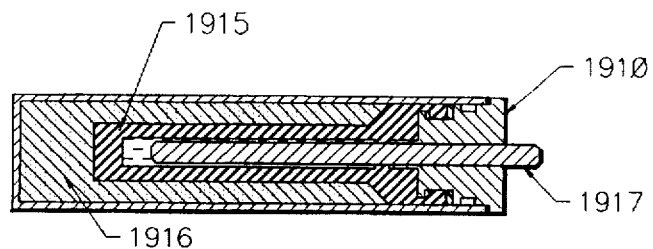
FIG. 19 is a sectional view of a thermal actuator according to another embodiment of the invention.

FIG. 19 illustrates another embodiment of the invention that does not incorporate the adjustable actuation temperature feature. The actuator body 1910 is fabricated by any suitable method such as deep drawing. Operation of this embodiment is identical to the operation of the embodiment shown in FIG. 12, except that the actuation temperature is determined by the type of material chosen as thermally responsive material 1916.

Figure 20:
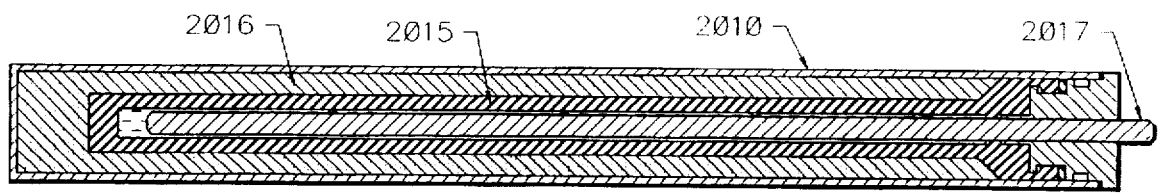
FIG. 20 is a sectional view of a thermal actuator according to still another embodiment of the invention.

FIG. 20 illustrates another embodiment of the invention with a long stroke. This embodiment is equivalent to the embodiment shown in FIG. 19, except that the actuator body 2010, the actuator boot 2015, and the actuator rod 2017 are longer. The long stroke is possible despite the potentially large frictional forces because of the self-lubricating, low durometer actuator boot 2015.

Figure 21:
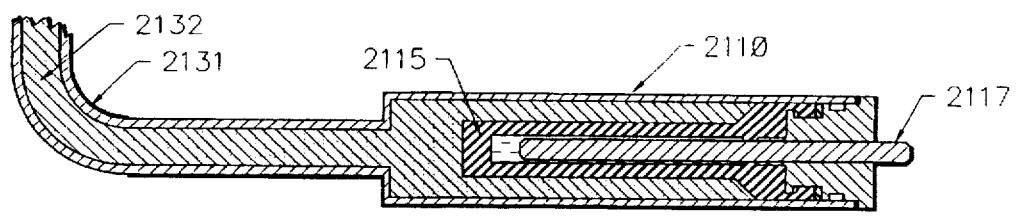
FIG. 21 is a sectional view of a thermal actuator according to yet another embodiment of the invention.

FIG. 21 illustrates another embodiment of the invention with a remote sensing capability. A hydraulic pressure line 2131 is attached to the actuator body 2110 and communicates freely with the enclosed volume. Hydraulic fluid 2132 can be any force-transmitting fluid, including a thermally responsive material. Hydraulic pressure generated from a remote sensing bulb filled with a thermally responsive fluid, or a hydraulic power source is transmitted through the hydraulic pressure line 2131 to the actuator. The hydraulic pressure causes extension of the actuator rod 2117 in an equivalent manner to the primary embodiment of the invention. This embodiment provides an inexpensive device for the conversion of hydraulic pressure to linear motion, with a minimum of power loss, hysterisis, and wear.

Figure 22:
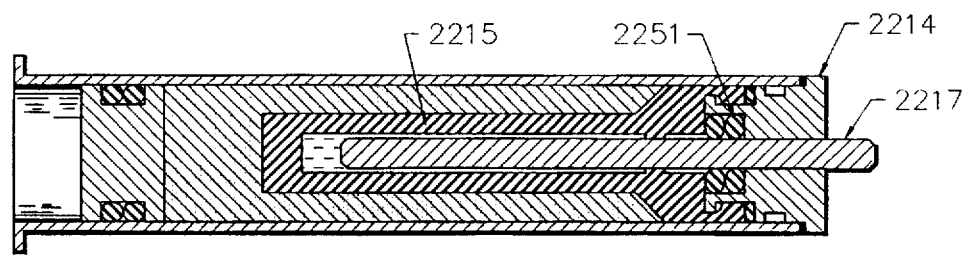
FIG. 22 is an expanded sectional view of a thermal actuator according to yet still another embodiment of the invention.
Figure 23:
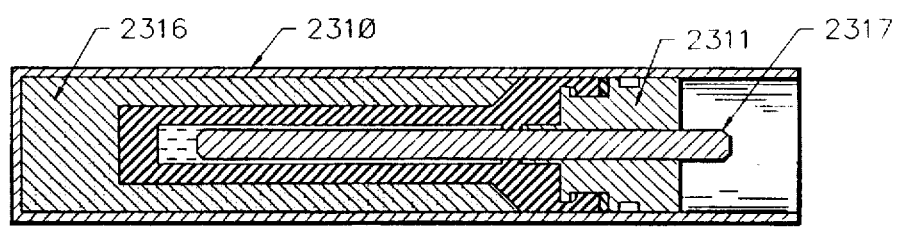
FIG. 23 is a sectional view of a thermal actuator according to another alternative embodiment of the invention.

FIG. 22 illustrates another embodiment of the invention designed for situation where an enhanced seal against water intrusion is required. The seal 2251 is placed in the actuator piston 2211 and held in place by the actuator boot 2215 such that hydraulic pressure holds the seal in place. It can be seen from FIG. 22 and FIG. 13 that assembly of such a device is straightforward. The seal O-ring 2251 is simply placed between the actuator plug 2214 and the actuator boot 2215 during the assembly process. The O-ring 2251 seals against pressures in excess of 500 psi.

Figure 24:
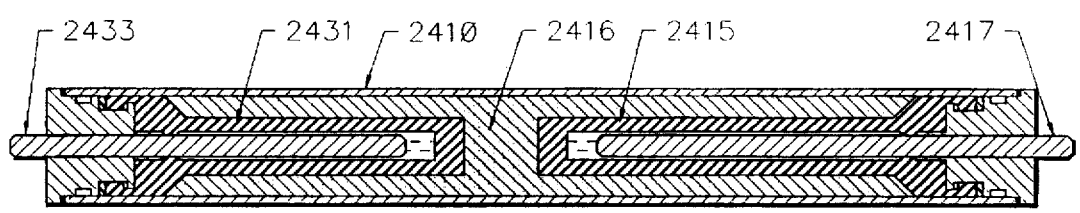
FIG. 24 is a sectional view of a thermal actuator according to yet another alternative embodiment of the invention.

FIG. 24 shows another embodiment of the invention in which the adjustable actuation temperature mechanism and the actuator rod 2417 are in the same end of the actuator body 2410. In this embodiment, the actuator piston 2411 is free to move relative to the actuator body 2410, increasing or decreasing the volume available for expansion of the thermally responsive material 2416, and thereby establishing the actuation temperature of the device. The actuator piston 2411 forms a tight seal with the actuator body 2410, while allowing movement by an O-ring type action on the actuator boot 2415. The position of the actuator piston 2411 relative to the actuator body 2410 can be established by any suitable means. It can be seen that this embodiment will operate in a similar manner to the embodiment illustrated in FIG. 6.

FIG. 24 shows another embodiment of the invention in which the adjustable actuation temperature capability is provided by another actuator boot/actuator plug/actuator rod configuration in the opposite end of the actuator. It can be seen from the illustration that as the second actuator rod 2433 is positioned relative to the actuator body 2410, the volume available for expansion of the thermally responsive material is increased or decreased, thereby adjusting the actuation temperature. The diameter of the second actuator rod 2433 is typically greater than the diameter of the first actuator rod 2417, thereby allowing temperature adjustment by relatively small movements of the actuator rod 2433. The position of the actuator rod 2433 relative to the actuator body 2410 can be established by any suitable means.

Figure 25:
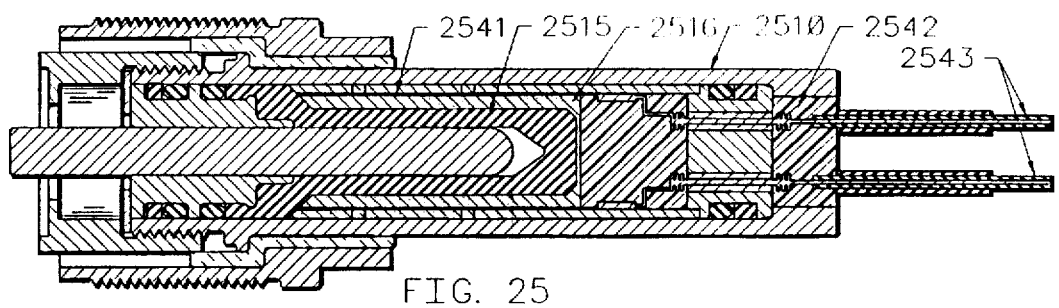
FIG. 25 is a sectional view of a solid state linear motor incorporating a thermal actuator according to the present invention.

FIG. 25 shows a thermostat element 2510 of the present invention incorporated into a solid state linear motor which converts electricity into useful mechanical work. The motor includes a heating element 2541, which is preferably a film type heating element providing high surface area for heat transfer and therefore low surface temperatures- The heating element 2541 is shown here to be located within the actuator tube 2510, although it may also be located externally of the tube. A feedthrough 2542 is mounted in the neck of the tube 2510, and a set of electrically conductive wires 2543 extend through the feedthrough 2542, joining the heating elements 2541 to an outside power source (not shown).

In operation, the flow of electricity through the heating elements 2541 causes the expansion material 2516 in the tube 2510 to expand, thereby squeezing the actuator boot 2515, and forcing the actuator rod 2517 to move outwardly, creating mechanical work. A linear motor incorporating the features of the present invention has several advantages over prior art motors in that it is resettable, has low power requirements, can generate output forces over 500 lbs, and has a gentle, smooth stroke of 3" or more. In addition, such a motor is highly reliable, since it requires only a single moving part. It is safe, can be fabricated from a variety of materials, can be magnetically cleaned, is small in size, and low in weight.

The tube 2510 of the actuator is designed to fail by stretching outward to internal pressures of two to three times the maximum working pressure of the actuator, and one half the pressure at which the seals fail. The expansion of the tube 2510 prevents the actuator from bursting or releasing material to the environment if left on continuously.

Figure 26A:
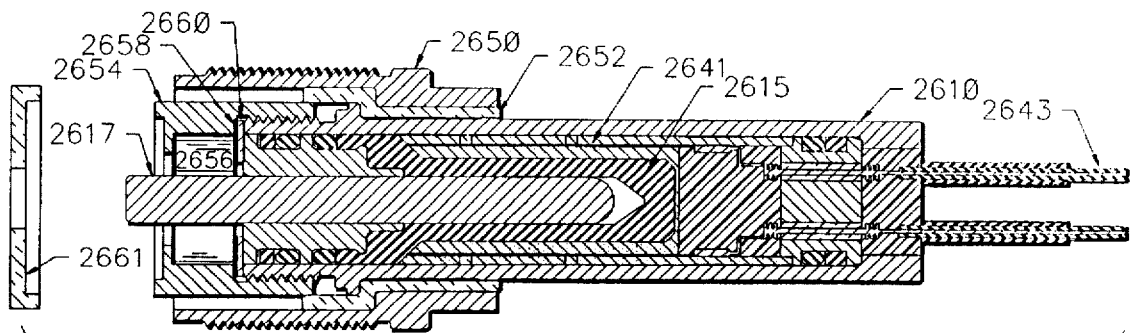
FIGS. 26A–B–C show another embodiment of the motor illustrated in FIG. 25.
Figure 26B:
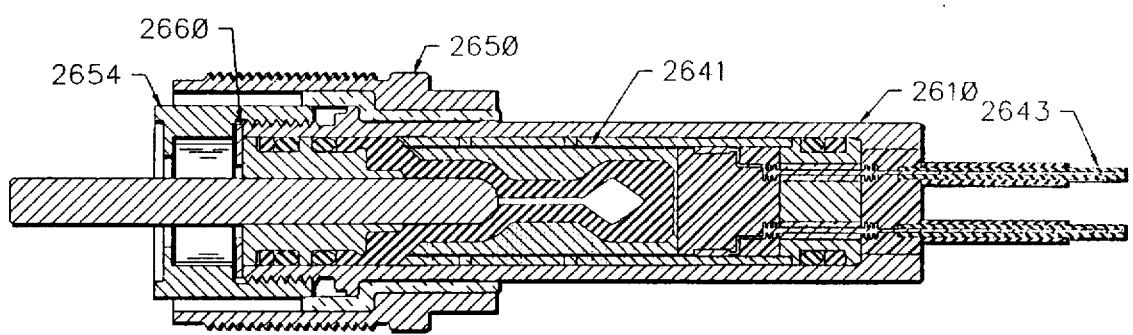
Figure 26C:
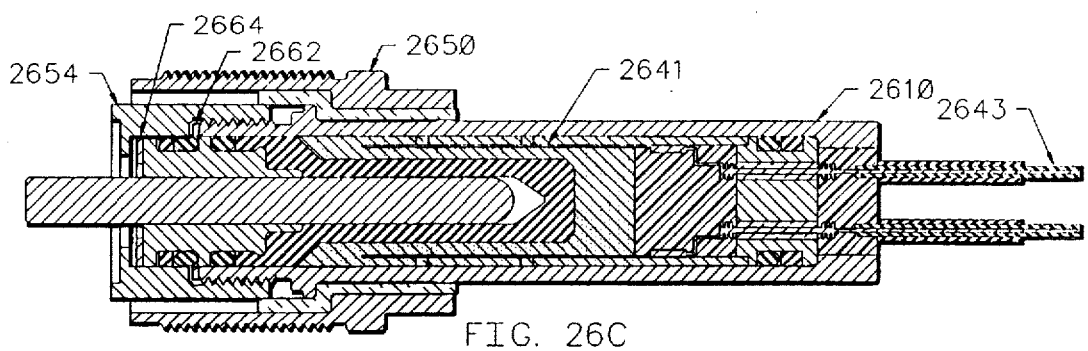
Figure 27A:
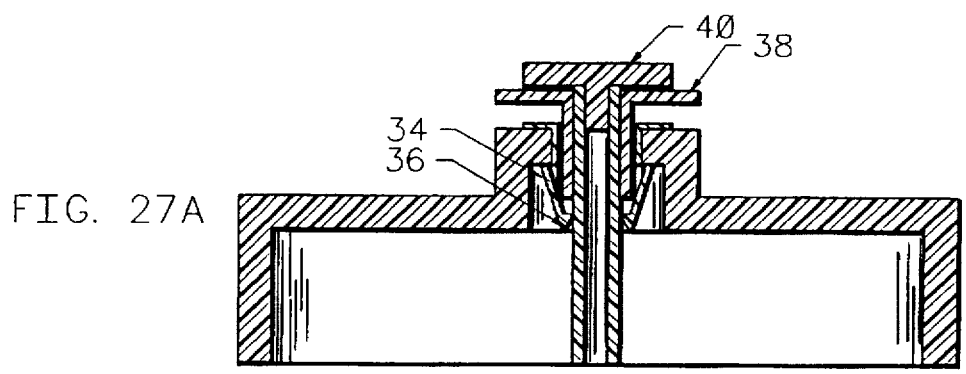
FIGS. 27 A–D show operation of an occlusion release system utilized in the infusion pump of FIG. 1.
Figure 27B:
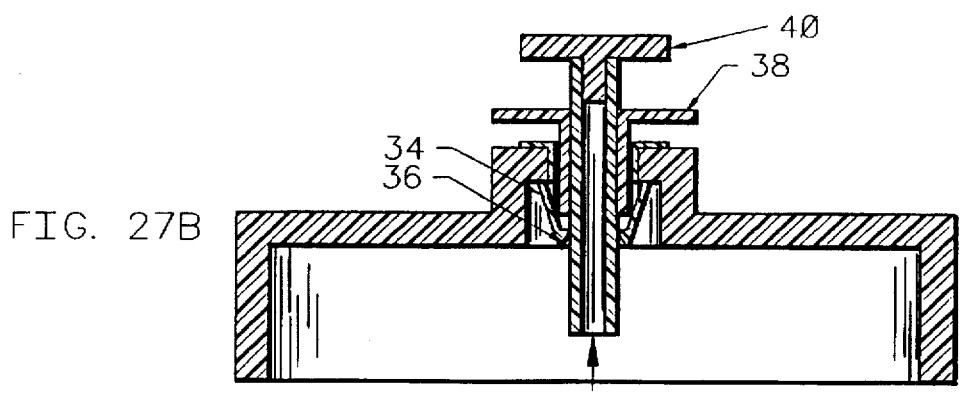
Figure 27C:
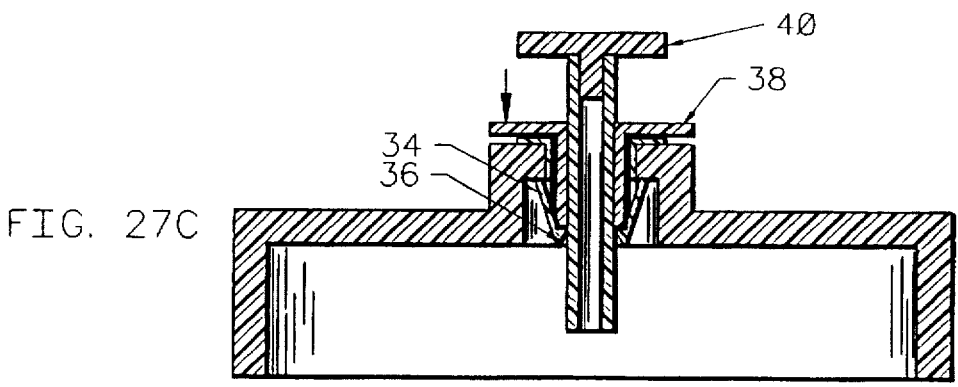
Figure 27D:
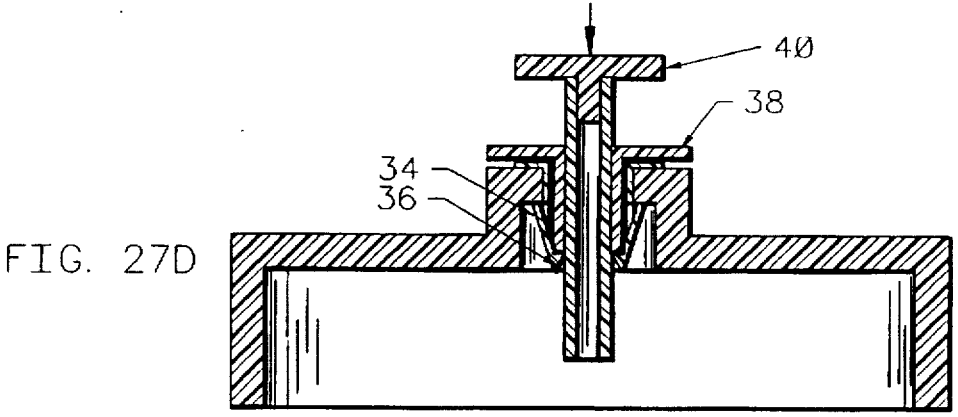

An alternate embodiment of the solid state linear motor is illustrated in FIGS. 26A–C. This embodiment is substantially similar to the embodiment of FIG. 25, except for the mode of failure. As in the previous embodiment, the motor includes a heating element 2641 which is coupled to a set of electrically conductive wires 2643 extending through a feedthrough 2642 in the rear of actuator tube 2610. Wires 2643 connect heating element 2641 to an outside power source (not shown).

An externally threaded mounting ferrule 2650 is carried at the front end of actuator tube 2610. A fiberglass insulator 2652 is disposed between the mounting ferrule 2650 and the front end of the tube 2610. An outer plug member 2654 is carried in an annular space between the front end of insulator 2652 and the front end of tube 2610. Plug member 2654 includes a bore 2656 surrounding actuation rod 2617 and a counterbore 2658 which encircles the end of tube 2610. A stainless steel shear disk 2660 is retained between the front end of tube 2610 and the front end of counterbore 2658. An optional fiberglass insulator is carried at the end of the mounting ferrule 2650.

In operation, the flow of electricity through heating elements 2641 causes the expansion material 2616 in tube 2610 to expand, thereby squeezing actuator boot 2615, and forcing actuation rod 2617 to move outwardly as shown in FIG. 26B. As long as rod 2617 is allowed to extend freely from the boot, the pressure within tube 2610 will remain at a reasonable level, and shear disk 2660 will prevent actuator plug 2614 from moving out. However, if any blockage were to prevent to constrain the movement of rod 2617, the pressure in tube 2610 would begin to increase. Once this pressure reaches a level of 9000 psi, shear disk 2660 is designed to fail. Thus, actuator plug 2614 moves outwardly, pushing the central portion 2662 of shear disk 2660 outwardly, while the outer rim 2664 of disk 2660 remains trapped between outer plug 2654 and the front end of tube 2610, as shown in FIG. 26C. The outward motion of actuator plug relieves the internal pressure in tube 2610, so that catastrophic failure does not occur.

Various changes and modifications to the embodiments herein chosen for purposes of illustration will readily occur to those skilled in the art. To the extent that such modifications and variations do not depart from the spirit of the invention, they are intended to be included within the scope thereof, which is limited only by a fair interpretation of the appended claims.

Having fully described and disclosed the instant invention in such clear and concise terms as to enable those skilled in the art to understand and practice the same, the claimed invention is set forth below.

What is claimed is:

1. A linear motor comprising:
   a) a thermal actuator, said actuator including;
      i) an actuator body defining a chamber and having opposite ends,
      ii) a force-transmitting elastomeric component disposed in said chamber, said elastomeric component being closed at one end and having a central bore of predetermined diameter through the opposite end, said elastomeric component having a wall of predetermined thickness and of a predetermined durometer rating, said actuator body including an annular wall encircling said elastomeric component in spaced relation thereto,
      iii) an actuation rod having an end portion reciprocably received in said bore, and
      iv) a thermally responsive expansion material contained between said elastomeric component and said encircling wall for squeezing said elastomeric component to force said actuation rod outwardly of said chamber; and
   b) heating means for causing said thermally responsive expansion material to expand, thereby producing linear motion from said actuation rod.

2. The linear motor of claim 1, in which said heating means comprises a film-type heating element.

3. The linear motor of claim 1, in which said actuator body comprises a radially expandable tube.

4. The linear motor of claim 3, in which said radially expandable tube is designed to withstand internal pressures up to at least two times the maximum working pressure of said actuator.

5. The linear motor of claim 1, in which said actuator further comprises sealing means for preventing intrusion of outside materials up to a predetermined failure pressure.

6. The linear motor of claim 5, in which said actuator body comprises a radially expandable tube designed to withstand internal pressures up to half of said predetermined failure pressure.

7. The linear motor of claim 1, in which said actuator further comprises adjustment means for adjusting the temperature at which said actuation rod begins to move, said adjustment means allowing adjustment to be performed repeatedly after assembly and installation of said thermal actuator.

8. The linear motor of claim 1, in which said actuation rod has a predetermined diameter substantially less than the predetermined diameter of said bore in said elastomeric component, thus creating an annular space of predetermined size between said rod and said elastomeric component, said annular space containing a lubricant.

9. The linear motor of claim 1, wherein the durometer rating and wall thickness of said elastomeric component and the size of the annular space between said rod and said elastomeric component have been selected such that when said thermally responsive expansion material exerts sufficient hydraulic pressure on said elastomeric component, said elastomeric component compresses radially to assume a creased configuration, defining a space for retaining lubricant along the length of said rod.

10. The linear motor of claim 8, in which the geometry of said end portion of said rod and of said elastomeric component when creased are selected to create a pocket of lubricant which follows the movement of said rod end.

11. The linear motor of claim 8, in which the geometry of said end portion of said rod and of said elastomeric component are selected to create a reservoir of lubricant at the closed end of said elastomeric component, said reservoir slowly shrinking due to compression set, thereby releasing said lubricant over time.

12. The linear motor of claim 1, in which said force-transmitting elastomeric component is formed from a high performance urethane.

13. The linear motor according to claim 1, further comprising:
   a) an actuator plug slidably mounted in said bore in the other end of said elastomeric component and encircling said actuation rod; and
   b) a rigid element fixedly secured to one end of said actuator body and juxtaposed against said actuator plug to prevent said plug from sliding outwardly in said chamber in response to normal internal pressures in said chamber, said element being designed to shear when said pressure reaches a predetermined threshold level, thus enabling said actuator plug to slide outwardly to relieve said pressure.

* * * * *